US011781697B2

(12) United States Patent
Furcoiu

(10) Patent No.: US 11,781,697 B2
(45) Date of Patent: *Oct. 10, 2023

(54) STENT SPRINGS AND STENTS FOR REPAIRING PIPES

(71) Applicant: Mueller International, LLC, Atlanta, GA (US)

(72) Inventor: Aurelian Ioan Furcoiu, Oswego, IL (US)

(73) Assignee: Mueller International, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/727,574

(22) Filed: Apr. 22, 2022

(65) Prior Publication Data

US 2022/0243854 A1 Aug. 4, 2022

Related U.S. Application Data

(62) Division of application No. 16/792,984, filed on Feb. 18, 2020, now Pat. No. 11,353,154.

(60) Provisional application No. 62/834,168, filed on Apr. 15, 2019, provisional application No. 62/807,264, filed on Feb. 19, 2019.

(51) Int. Cl.
*F16L 55/18* (2006.01)
*F16L 55/17* (2006.01)
(52) U.S. Cl.
CPC .............. *F16L 55/18* (2013.01); *F16L 55/17* (2013.01)
(58) Field of Classification Search
CPC .................................. F16L 55/18; F16L 55/17
USPC .......................................................... 138/99
See application file for complete search history.

(56) References Cited

U.S. PATENT DOCUMENTS

| 3,656,771 | A | 4/1972 | Stout |
| 3,895,652 | A | 7/1975 | Zach |
| 4,426,095 | A | 1/1984 | Buttner |
| 4,589,447 | A | 5/1986 | Kane et al. |
| 4,647,072 | A | 3/1987 | Westman |
| 4,927,189 | A | 5/1990 | Burkit |
| 5,035,539 | A | 7/1991 | Kawafuji et al. |
| 5,119,862 | A | 6/1992 | Maimets et al. |
| 5,351,720 | A | 10/1994 | Maimets |
| 5,624,124 | A | 4/1997 | Ungchusri et al. |

(Continued)

FOREIGN PATENT DOCUMENTS

| EP | 0239930 | 10/1987 |
| EP | 0621015 | 10/1994 |

(Continued)

OTHER PUBLICATIONS

US 11,035,513 B2, 06/2021, Furcoiu (withdrawn)

(Continued)

*Primary Examiner* — Craig M Schneider
*Assistant Examiner* — David R Deal
(74) *Attorney, Agent, or Firm* — Taylor English Duma LLP

(57) ABSTRACT

A stent spring for repairing a pipe includes a substantially tubular mesh structure comprising one or more strands, the one or more strands comprising a spring material, wherein the stent spring is expandable and compressible between an expanded configuration and a compressed configuration; and an elastic wire connected to the one or more strands, the elastic wire configured to increase a flexibility of the stent spring.

21 Claims, 20 Drawing Sheets

(56) References Cited

U.S. PATENT DOCUMENTS

| | | |
|---|---|---|
| 6,200,336 B1 | 3/2001 | Pavcnik et al. |
| 6,270,524 B1 | 8/2001 | Kim |
| 6,375,677 B1 | 4/2002 | Penn et al. |
| 6,589,275 B1 | 7/2003 | Ivancev et al. |
| 6,712,556 B2 | 3/2004 | Penza |
| 6,820,653 B1 | 11/2004 | Schempf et al. |
| 7,025,580 B2 | 4/2006 | Heagy et al. |
| 7,172,370 B2 | 2/2007 | Schmidt |
| 7,267,141 B1 | 9/2007 | De Meyer et al. |
| 7,918,882 B2 | 4/2011 | Pavcnik et al. |
| 8,230,913 B2 | 7/2012 | Hart et al. |
| 8,488,290 B2 | 7/2013 | Kauffman |
| 8,783,297 B2 | 7/2014 | Hawwa et al. |
| 9,052,051 B2 | 6/2015 | Maimets et al. |
| 10,143,552 B2 | 12/2018 | Wallace et al. |
| 10,245,167 B2 | 4/2019 | Longo |
| 10,368,990 B2 | 8/2019 | Noe et al. |
| 10,641,427 B2 | 5/2020 | Braun et al. |
| 11,079,058 B2 | 8/2021 | Furcoiu |
| 11,187,366 B2 | 11/2021 | Furcoiu |
| 11,221,099 B2 | 1/2022 | Braun et al. |
| 11,326,731 B2 | 5/2022 | Furcoiu |
| 11,353,154 B2 | 6/2022 | Furcoiu |
| 11,391,405 B2 | 7/2022 | Furcoiu |
| 11,480,286 B2 | 10/2022 | Furcoiu |
| 2002/0144822 A1 | 10/2002 | Hackworth et al. |
| 2003/0017775 A1 | 1/2003 | Sowinski et al. |
| 2003/0040791 A1 | 2/2003 | Oktay |
| 2003/0233140 A1 | 12/2003 | Hartley et al. |
| 2004/0236398 A1 | 11/2004 | Burgmeier et al. |
| 2005/0212220 A1 | 9/2005 | Graham |
| 2008/0140178 A1 | 6/2008 | Rasmussen et al. |
| 2008/0255660 A1 | 10/2008 | Guyenot et al. |
| 2008/0269789 A1 | 10/2008 | Eli |
| 2009/0248132 A1* | 10/2009 | Bloom .................. A61F 2/2418 623/1.15 |
| 2010/0010617 A1 | 1/2010 | Goodson Iv et al. |
| 2010/0049313 A1 | 2/2010 | Alon et al. |
| 2010/0263759 A1 | 10/2010 | Maimets et al. |
| 2011/0264186 A1 | 10/2011 | Berglung et al. |
| 2012/0273078 A1 | 11/2012 | Hawwa et al. |
| 2013/0018450 A1 | 1/2013 | Hunt |
| 2013/0131783 A1 | 5/2013 | Shalev et al. |
| 2013/0158646 A1 | 6/2013 | Roeder |
| 2013/0248042 A1 | 9/2013 | Charest |
| 2016/0120638 A1 | 5/2016 | Michalak |
| 2016/0143732 A1 | 5/2016 | Glimsdale |
| 2016/0238178 A1 | 8/2016 | Urbanski |
| 2017/0231765 A1 | 8/2017 | Desrosiers et al. |
| 2017/0304092 A1 | 10/2017 | Hong et al. |
| 2019/0093813 A1 | 3/2019 | Badger et al. |
| 2019/0301657 A1 | 10/2019 | Braun et al. |
| 2020/0224811 A1 | 7/2020 | Braun et al. |
| 2020/0263823 A1 | 8/2020 | Furcoiu |
| 2020/0292119 A1 | 9/2020 | Furcoiu |
| 2020/0292120 A1 | 9/2020 | Furcoiu |
| 2020/0318765 A1 | 10/2020 | Bechler |
| 2020/0340610 A1 | 10/2020 | Furcoiu |
| 2020/0378542 A1 | 12/2020 | Eitel |
| 2021/0041051 A1 | 2/2021 | Furcoiu |
| 2021/0041052 A1 | 2/2021 | Furcoiu |
| 2021/0381637 A1 | 12/2021 | Furcoiu |
| 2022/0228691 A1 | 7/2022 | Furcoiu |
| 2022/0228692 A1 | 7/2022 | Furcoiu |

FOREIGN PATENT DOCUMENTS

| | | |
|---|---|---|
| GB | 2471579 | 1/2011 |
| JP | 2005278993 | 10/2005 |
| KR | 1020070018627 | 2/2007 |
| WO | 2011001189 | 1/2011 |
| WO | 2019194870 | 10/2019 |
| WO | 2020172136 | 8/2020 |
| WO | 2020219294 | 10/2020 |

OTHER PUBLICATIONS

US 11,131,417 B2, 09/2021, Braun et al. (withdrawn)

Braun, Clifton; Non-Final Office Action for U.S. Appl. No. 16/112,207, filed Aug. 24, 2018, dated Nov. 5, 2019, 14 pgs.

Braun, Clifton; Notice of Allowance for U.S. Appl. No. 16/112,207, filed Aug. 24, 2018, dated Feb. 13, 2020, 13 pgs.

Braun, Clifton; Corrected Notice of Allowance for U.S. Appl. No. 16/836,468, filed Mar. 31, 2020, dated Aug. 31, 2021, 6 pgs.

Braun, Clifton; Non-Final Office Action for U.S. Appl. No. 16/836,468, filed Mar. 31, 2020, dated May 20, 2021, 29 pgs.

Braun, Clifton; Notice of Allowance for U.S. Appl. No. 16/836,468, filed Mar. 31, 2020, dated Oct. 1, 2021, 9 pgs.

Braun, Clifton; Notice of Allowance for U.S. Appl. No. 16/836,468, filed Mar. 31, 2020, dated Aug. 12, 2021, 13 pgs.

Furcoiu, Aurelian Ioan; Examiner-Initiated Interview Summary for U.S. Appl. No. 16/845,557, filed Jan. 10, 2020, dated Apr. 21, 2021, 2 pgs.

Furcoiu, Aurelian Ioan; Non-Final Office Action for U.S. Appl. No. 16/845,557, filed Apr. 10, 2020, dated Aug. 17, 2021, 35 pgs.

Furcoiu, Aurelian Ioan; Notice of Allowance for U.S. Appl. No. 16/845,557, filed Apr. 10, 2020, dated Jan. 11, 2022, 17 pgs.

Furcoiu, Aurelian Ioan; Final Office Action for U.S. Appl. No. 16/792,984, filed Feb. 18, 2020, dated Nov. 24, 2021, 15 pgs.

Furcoiu, Aurelian Ioan; Non-Final Office Action for U.S. Appl. No. 16/792,984, filed Feb. 18, 2020, dated May 25, 2021, 25 pgs.

Furcoiu, Aurelian Ioan; Notice of Allowance for U.S. Appl. No. 16/792,984, filed Feb. 28, 2020, dated Jan. 31, 2022, 9 pgs.

Furcoiu, Aurelian Ioan; Requirement for Restriction/Election for U.S. Appl. No. 17/792,984, filed Feb. 18, 2020, dated Apr. 1, 2021, 6 pgs.

Furcoiu, Aurelian Ioan; Corrected Notice of Allowance for U.S. Appl. No. 16/786,193, filed Feb. 10, 2020, dated May 17, 2021, 6 pgs.

Furcoiu, Aurelian Ioan; Corrected Notice of Allowance for U.S. Appl. No. 16/786,193, filed Feb. 10, 2020, dated Jun. 22, 2021, 6 pgs.

Furcoiu, Aurelian Ioan; Non-Final Office Action for U.S. Appl. No. 16/786,193, filed Feb. 10, 2020, dated Feb. 4, 2021, 22 pgs.

Furcoiu, Aurelian Ioan; Notice of Allowance for U.S. Appl. No. 16/786,193, filed Feb. 10, 2020, dated Apr. 26, 2021, 9 pgs.

Furcoiu, Aurelian Ioan; Corrected Notice of Allowance for U.S. Appl. No. 16/786,246, filed Feb. 10, 2020, dated Aug. 31, 2021, 6 pgs.

Furcoiu, Aurelian Ioan; Corrected Notice of Allowance for U.S. Appl. No. 16/786,246, filed Feb. 10, 2020, dated Aug. 6, 2021, 7 pgs.

Furcoiu, Aurelian Ioan; Non-Final Office Action for U.S. Appl. No. 16/786,246, filed Feb. 10, 2020, dated Mar. 4, 2021, 21 pgs.

Furcoiu, Aurelian Ioan; Notice of Allowance for U.S. Appl. No. 16/786,246, filed Feb. 10, 2020, dated Oct. 14, 2021, 9 pgs.

Furcoiu, Aurelian Ioan; Requirement for Restriction/Election for U.S. Appl. No. 16/786,246, filed Feb. 10, 2020, dated Feb. 3, 2021, 6 pgs.

Braun, Clifton; International Preliminary Report on Patentability for PCT Application No. PCT/US 18/63325, filed Nov. 30, 2018, dated Oct. 15, 2020, 7 pgs.

Braun, Clifton; International Search Report for PCT Application No. PCT/US 18/63325, filed Nov. 30, 2018, dated Feb. 5, 2019, 8 pgs.

Braun, Cliff; Extended European Search report for application No. 18913510.6, filed Nov. 30, 2018, dated Sep. 13, 2021, 7 pgs.

Furcoiu, Aurelian Ioan; International Preliminary Report on Patentability for PCT Application No. PCT/US20/28038, filed Apr. 14, 2020, dated Nov. 4, 2021, 8 pgs.

Furcoiu, Aurelian Ioan; International Search Report and Written Opinion for PCT Application No. PCT/US20/28038, filed Apr. 14, 2020, dated Jun. 24, 2020, 9 pgs.

Furcoiu, Aurelian Ioan; International Preliminary Report on Patentability for PCT Application No. PCT/US20/18593, filed Feb. 18, 2020, dated Sep. 2, 2021, 8 pgs.

(56) References Cited

OTHER PUBLICATIONS

Furcoiu, Aurelian Ioan; International Search Report and Written Opinion for PCT Application No. PCT/US20/18593, filed Feb. 18, 2020, dated May 7, 2020, 9 pgs.

Furcoiu, Aurelian Ioan; Non-Final Office Action for U.S. Appl. No. 16/987,067, filed Aug. 6, 2020, dated Dec. 7, 2021, 32 pgs.

Furcoiu, Aurelian Ioan; Notice of Allowance for U.S. Appl. No. 16/987,067, filed Aug. 6, 2020, dated Apr. 5, 2022, 13 pgs.

Furcoiu, Aurelian Ioan; Notice of Allowance for U.S. Appl. No. 17/407,374, filed Aug. 20, 2021, dated Sep. 12, 2022, 37 pgs.

Furcoiu, Aurelian Ioan; Extended European Search Report for application No. 20758706.4, filed Feb. 18, 2020, dated Nov. 16, 2022, 9 pgs.

Furcoiu, Aurelian Ioan; Extended European Search Report for application No. 22204247.5, filed Feb. 18, 2020, dated Jan. 5, 2023, 7 pgs.

Furcoiu, Aurelian Ioan; Non-Final Office Action for U.S. Appl. No. 16/987,106, filed Aug. 6, 2020, dated Mar. 27, 2023, 61 pgs.

Furcoiu, Aurelian Ioan; Requirement for Restriction/Election for U.S. Appl. No. 16/987,106, filed Aug. 6, 2020, dated Feb. 9, 2023, 10 pgs.

Braun, Clifton; Extended European Search Report for application No. 23179851.3, filed Nov. 30, 2018, dated Jul. 6, 2023, 7 pgs.

Furcoiu, Aurelian Ioan; Notice of Allowance for U.S. Appl. No. 16/987,106, filed Aug. 6, 2020, dated Jun. 22, 2023, 9 pgs.

\* cited by examiner

STENT SPRINGS AND STENTS FOR REPAIRING PIPES

CROSS-REFERENCE TO RELATED APPLICATIONS

The present application is a divisional of U.S. application Ser. No. 16/792,984, filed Feb. 18, 2020, which claims the benefit of U.S. Provisional Application No. 62/807,264, filed Feb. 19, 2019, and U.S. Provisional Application No. 62/834,168, filed Apr. 15, 2019, all of which are hereby specifically incorporated by reference herein in their entireties.

TECHNICAL FIELD

This disclosure relates to the field of pipe repair. More specifically, this disclosure relates to stent springs and stents for repairing a pipe.

BACKGROUND

Piping systems, including municipal water systems, can develop breaks in pipe walls that can cause leaking. Example of breaks in a pipe wall can include radial cracks, axial cracks, point cracks, etc. Repairing a break in a pipe wall often requires the piping system to be shut off, which can be inconvenient for customers and costly for providers. Further, repairs can necessitate grandiose construction, including the digging up of streets, sidewalks, and the like, which can be costly and time-consuming.

SUMMARY

It is to be understood that this summary is not an extensive overview of the disclosure. This summary is exemplary and not restrictive, and it is intended neither to identify key or critical elements of the disclosure nor delineate the scope thereof. The sole purpose of this summary is to explain and exemplify certain concepts off the disclosure as an introduction to the following complete and extensive detailed description.

Disclosed in a stent spring for repairing a pipe can comprising a substantially tubular mesh structure defining a void, the void defining a central axis, the mesh structure comprising one or more strands, the one or more strands defining a plurality of openings, wherein the stent spring is configurable in an expanded stent spring configuration and a compressed stent spring configuration; and a tab extending radially inward from the mesh structure into the void, the tab defining a tab opening.

Also disclosed is a stent spring for repairing a pipe comprising a substantially tubular mesh structure comprising one or more strands, the one or more strands comprising a spring material, wherein the stent spring is expandable and compressible between an expanded stent spring configuration and a compressed stent spring configuration; and an elastic wire connected to the one or more strands, the elastic wire configured to increase a flexibility of the stent spring.

A method for retaining a stent in a compressed configuration is also disclosed, the method comprising providing a stent, the stent comprising a stent spring, a seal, and a tab extending radially inward from the stent spring; biasing the stent to a compressed configuration; and engaging the tab with a compression mechanism to retain the stent in the compressed configuration.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

DETAILED DESCRIPTION

Figure 1A:
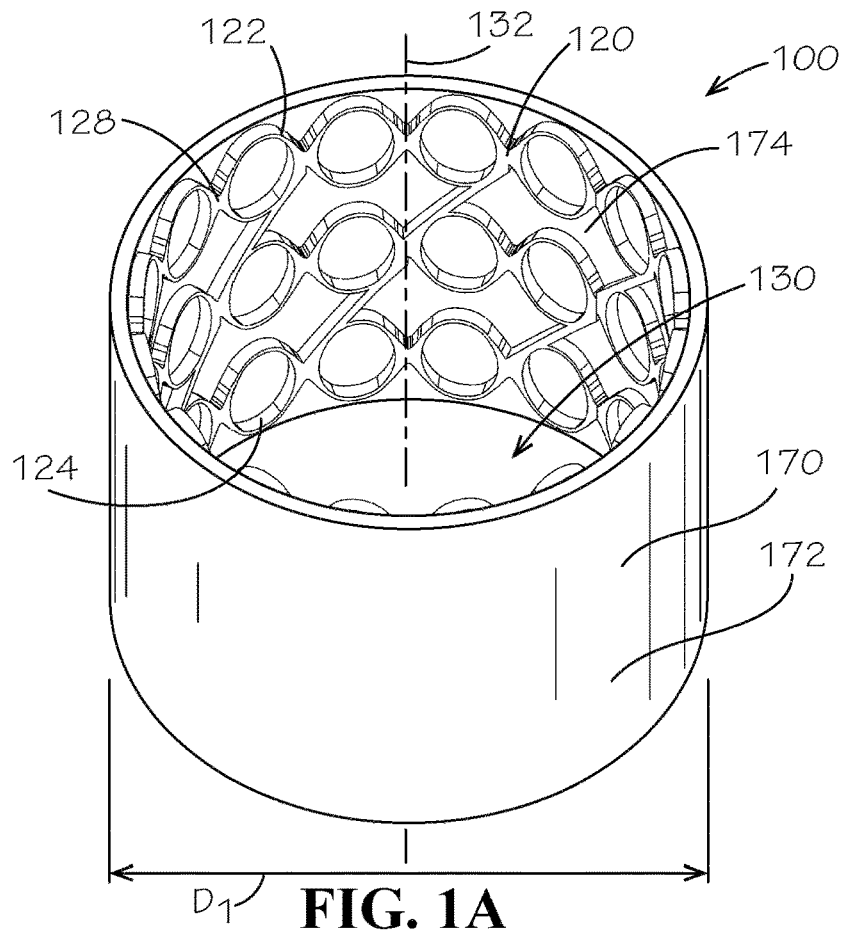
FIG. 1A is a top perspective view of a stent, in accordance with one aspect of the present disclosure, comprising a stent spring and a seal.

The present disclosure can be understood more readily by reference to the following detailed description, examples, drawings, and claims, and the previous and following description. However, before the present devices, systems, and/or methods are disclosed and described, it is to be understood that this disclosure is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description is provided as an enabling teaching of the present devices, systems, and/or methods in its best, currently known aspect. To this end, those skilled in the relevant art will recognize and appreciate that many changes can be made to the various aspects of the present devices, systems, and/or methods described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to "an element" can include two or more such elements unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

For purposes of the current disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific aspect or combination of aspects of the disclosed methods.

Disclosed in the present application is a stent for repairing a pipe, and associated methods, systems, devices, and various apparatus. Example aspects of the stent can be oriented in an expanded configuration and a compressed configuration. The stent can comprise a stent spring and a seal. Example aspects of the stent spring can define a tubular mesh structure comprising one or more strands. It would be understood by one of skill in the art that the disclosed stent is described in but a few exemplary aspects among many. No particular terminology or description should be considered limiting on the disclosure or the scope of any claims issuing therefrom.

Figure 25:
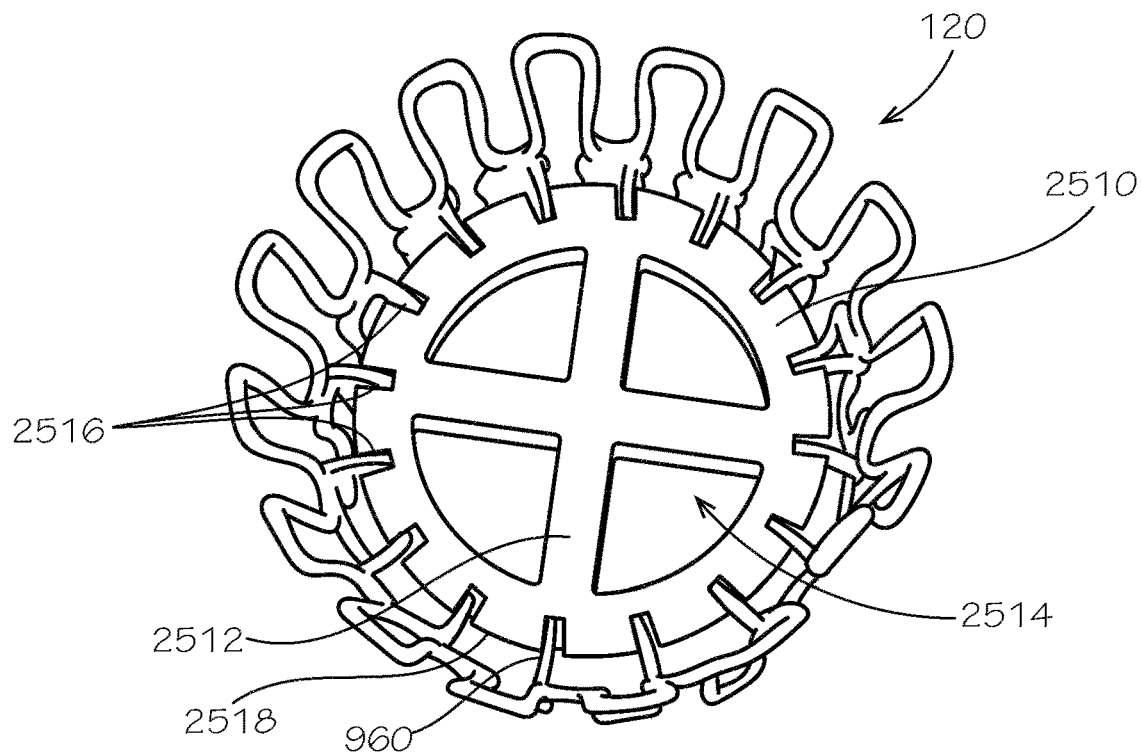
FIG. 25 is a top view of the stent spring retained in a compressed stent spring configuration by a compression mechanism.

FIG. 1A illustrates a first aspect of a stent 100 according to the present disclosure. As shown, the stent 100 can comprise a stent spring 120 and a seal 170. Example aspects of the stent spring 120 can define a spring force and can be expandable and compressible, such that the stent spring 120 can be oriented in an expanded stent spring configuration, as shown in FIG. 1A, and a compressed stent spring configuration, as shown in FIG. 25. As such, the stent 100 itself can also be oriented in an expanded configuration and a compressed configuration. According to example aspects, the stent 100 can be expanded within a pipe (not shown) such that the seal 170 can engage an inner wall (not shown) of the pipe where a crack or other damage is present, in order to create a watertight seal between the stent 100 and the inner wall of the pipe to prevent leaking at the damage site.

As shown in FIG. 1A, the stent spring 120 can bias the stent 100 to the expanded configuration. In the depicted aspect, the stent spring 120 can be formed as a substantially tubular mesh structure defining opposing open ends (e.g. a top end 122 and a bottom end 124). The stent spring 120 can further define an outer surface 126 (shown in FIG. 1B) and an opposite inner surface 128. The inner surface 128 can define a void 130. The void 130 can extend between the open top and bottom ends 122,124 of the stent spring 120, and can allow fluid to pass therethrough when the stent 100 is received in the pipe. A central axis 132 can extend substantially through a center of the void 130, as shown. According to example aspects, the stent spring 120 can be formed from a spring material. For example, the stent spring 120 can comprise a metal material, such as stainless steel, spring steel, aluminum, nitinol, cobalt chromium, or any other suitable material. In other aspects, the stent spring 120 can be formed from a plastic material, such as, for example, nylon, POM (polyoxymethylene), or PVC (polyvinyl chloride). In still another aspect, the stent spring 120 can be formed from a carbon fiber material. Optionally, the material can be an NSF certified material that can comply with various public health safety standards. For example, in some aspects, the material can be approved as safe for use in drinking-water applications. Moreover, in some aspects, the stent spring 120 can comprise a coating, such as, for example, a rubber or liquid metal coating. The coating can improve mechanical properties of the stent spring 120. For example, the coating can improve the tensile strength of the stent spring 120 by providing a flexible and/or springy outer layer. In some aspects, the coating can also be corrosion resistant, or a separate coating can be applied for corrosion resistance. For example, a corrosion resistant coating can comprise a zinc-nickel material, phosphate, electrophoretic paint (e-coating), polyester, fusion-bonded epoxy (FBE), or any other suitable corrosion resistant material.

Example aspects of the seal 170 can be formed as a continuous, tubular sleeve structure, as shown, and can define an outer surface 172 and an inner surface 174. In the present aspect, the outer surface 172 of the seal 170 can define a stent diameter $D_1$ of the stent 100. Example aspects of the seal 170 can comprise a flexible and compressible material, such as, for example, neoprene. In other aspects, the seal 170 can be formed from another synthetic rubber material such as EPDM rubber, natural rubber, foam, epoxy, silicone, a resin-soaked cloth, or any other suitable flexible material for providing a watertight seal between the stent 100 and the inner wall of the pipe. According to example aspects, the seal 170 can wrap around a circumference of the stent spring 120, and the inner surface 174 of the seal 170 can engage the outer surface 126 of the stent spring 120. In a particular aspect, the seal 170 can cover the entire outer surface 126 of the stent spring 120, as shown. However, in other aspects, the seal 170 can cover only a portion of the outer surface 126 of the stent spring 120. In still other aspects, the seal 170 may not wrap entirely around the circumference of the stent spring 120. In the present aspect, the seal 170 can fit snugly on the stent spring 120. In some aspects, the seal 170 can be coupled to the stent spring 120 by a fastener (not shown), such as, for example, stitching, adhesives, ties, or any other suitable fastener known in the art.

In the expanded configuration of the stent 100, as shown in FIG. 1A, the spring force of the stent spring 120 can bias the stent spring 120 and the seal 170 radially outward relative to the central axis 132, such that each of the stent spring 120 and seal 170 can define relatively concentric tubular shapes, as shown. In the expanded configuration, the stent 100 can define its largest possible stent diameter $D_1$. In some aspects, in the expanded configuration, the stent diameter $D_1$ can be slightly greater than an inner pipe diameter as defined by the inner wall of the pipe to aid in retaining the stent 100 against the inner wall.

In the compressed configuration, a compression force (i.e., a pushing force, a pulling force, or any other suitable force) can be applied to the stent 100 by a compression mechanism to bias the stent 100, including the stent spring 120 and the seal 170, to the compressed configuration. Various example aspects of such the compression mechanism are described through the present application, including, for example, an internal compression disc 2510 (shown in FIG. 25). The compression force can overcome the spring force, and the seal 170 and stent spring 120 can compress or fold radially inward towards the void 130 to define a smaller stent diameter $D_1$ and a smaller overall stent volume than in the expanded configuration. The reduced stent diameter $D_1$ and stent volume in the compressed configuration can allow for easier insertion of the stent 100 into the pipe or a pipeline (not shown) and easier navigation of the stent 100 through the pipe or pipeline. When the compression force is removed or reduced to less than the spring force, the stent spring 120 can bias the stent 100 back to the expanded configuration.

Figure 1B:
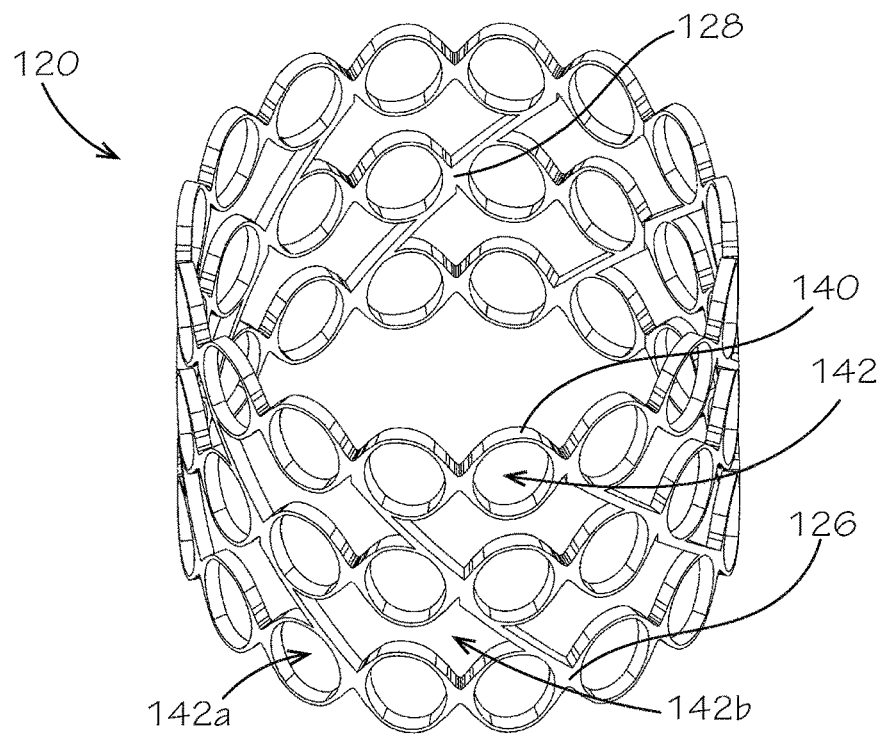
FIG. 1B is a top perspective view of the stent spring of FIG. 1A.
Figure 2:
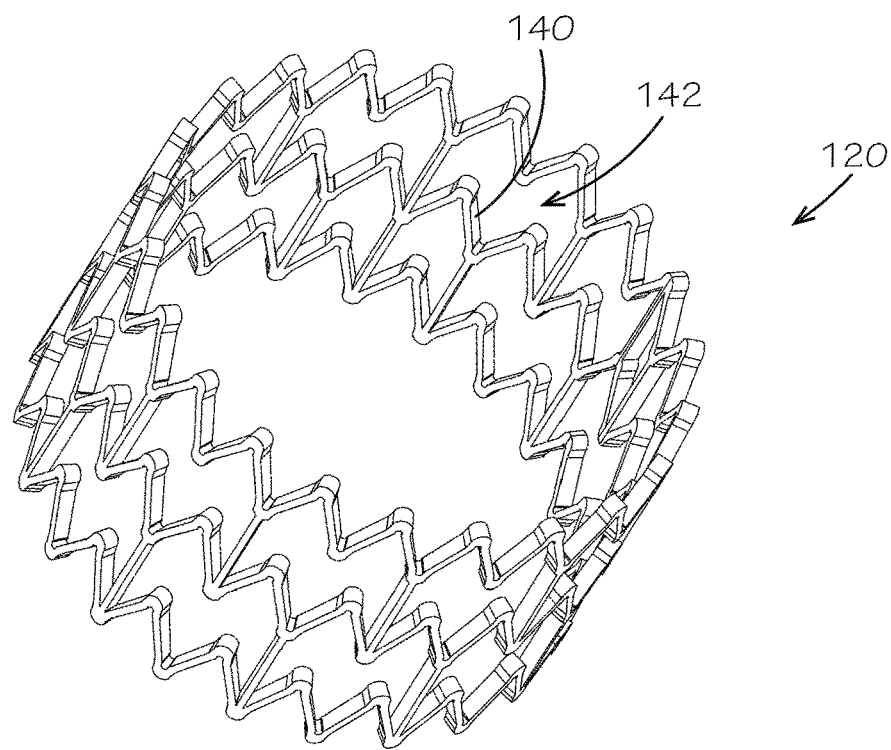
FIG. 2 is a top perspective view of the stent spring, in accordance with another aspect of the present disclosure.
Figure 3:
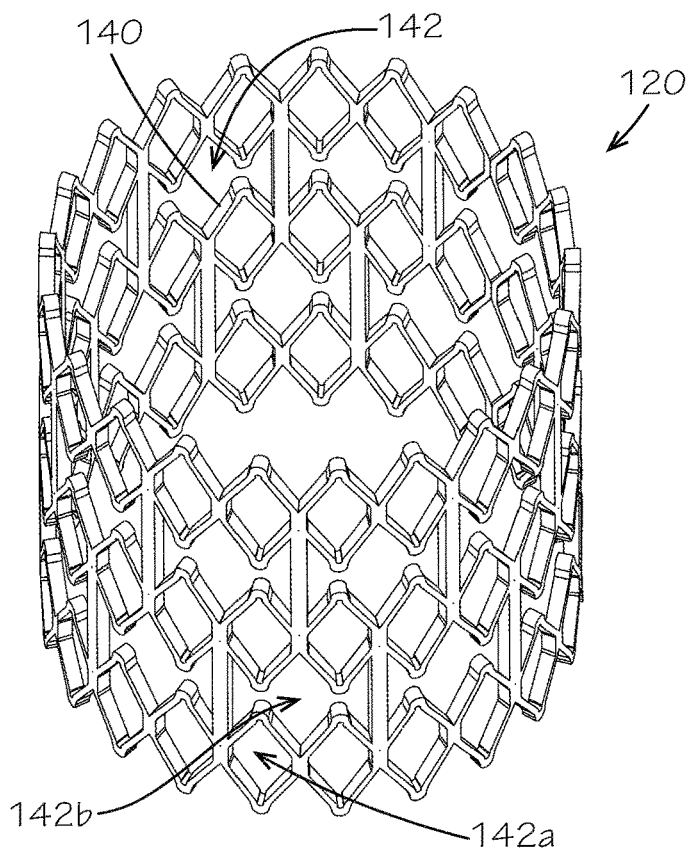
FIG. 3 is a top perspective view of the stent spring, in accordance with another aspect of the present disclosure.

FIG. 1B illustrates the stent spring 120 of FIG. 1A with the seal 170 (shown in FIG. 1A) removed for full visibility of the of the stent spring 120. As shown, the tubular mesh structure of the stent spring 120 can comprise one or more strands 140 arranged to define a plurality of openings 142 therebetween. In the present aspect, as shown, a plurality of the openings 142a can define a substantially circular shape, while other openings 142b can define a shape that is substantially that of a pair of conjoined diamonds. In other aspects, the openings 142 can define any other suitable shape(s), some examples of which are described below. According to example aspects, the mesh structure of the stent spring 120 can be laser cut, chemically etched, or stamped from a sheet of material (e.g., a sheet of metal). In other aspects, the mesh structure of the stent spring 120 can be formed by stereolithography (e.g., 3D printing), or by any other suitable manufacturing method suitable for forming a mesh structure. In some example aspects, the stent spring 120 can be oriented in a rolled configuration for use, as shown, and an unrolled configuration, as shown in FIG. 4B. In example aspects, the stent spring 120 can be manufactured in the unrolled configuration, and rolled into the rolled configuration thereafter for use. FIGS. 2 and 3 each illustrate an additional example aspect of the stent spring 120 in the rolled configuration. As shown in the aspect of FIG. 2, some or all of the openings 142 can substantially define an M-shape. As shown in the aspect of FIG. 3, some of the openings 142a can substantially define a diamond shape, and some other openings 142b can substantially define a series of conjoined diamond and half-diamond shapes.

Figure 4A:
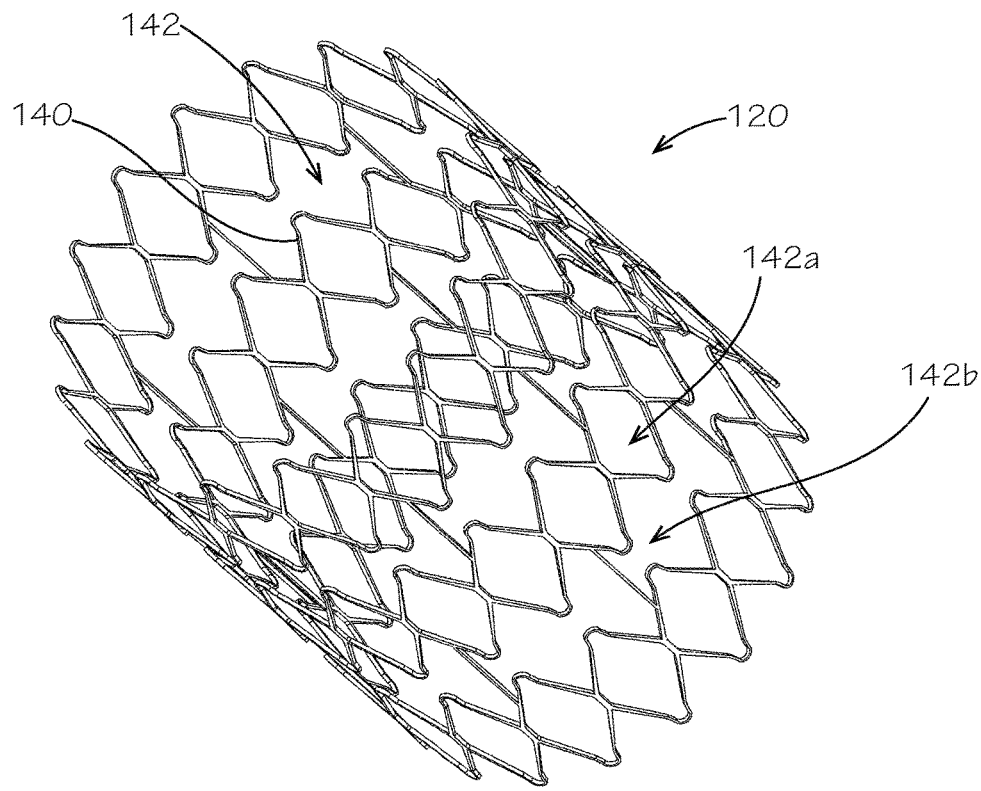
FIG. 4A is a perspective view of the stent spring, in accordance with another aspect of the present disclosure, wherein the stent spring is in a rolled configuration.
Figure 4B:
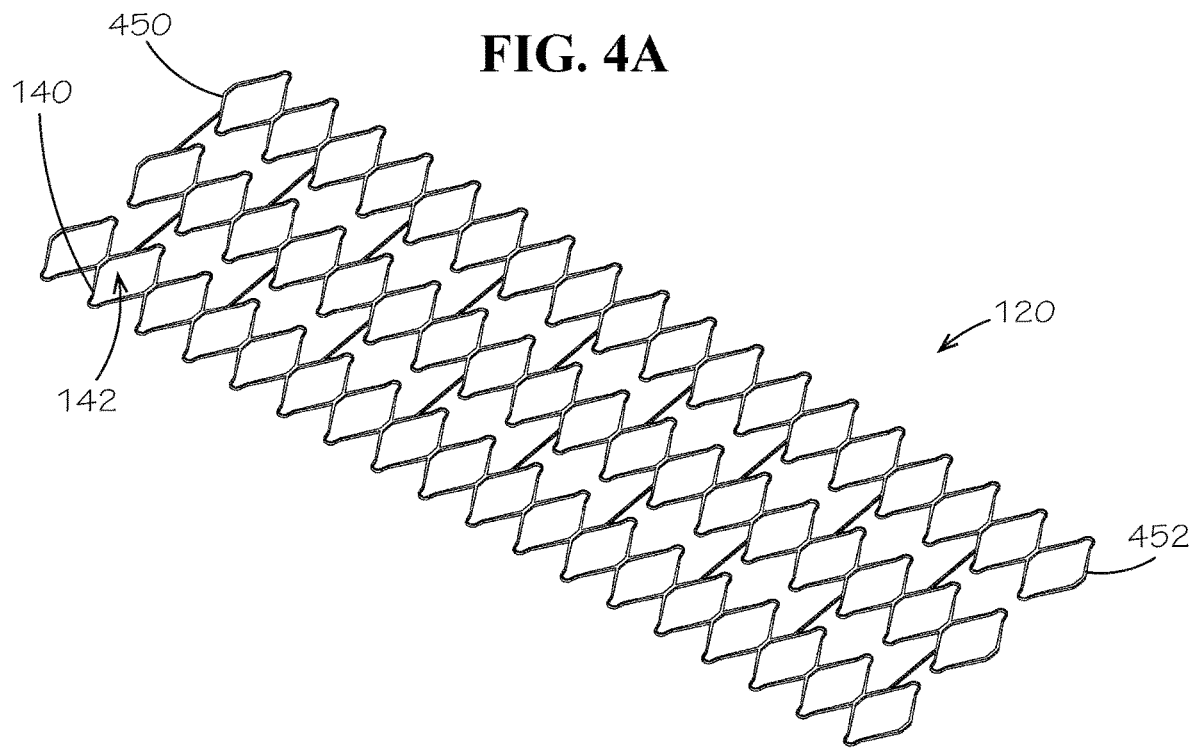
FIG. 4B is perspective view of the stent spring of FIG. 4A, wherein the stent spring is in an unrolled configuration.

FIG. 4A illustrates the stent spring 120 in the rolled configuration, according to another aspect of the present disclosure, and FIG. 4B illustrates the stent spring 120 of FIG. 4A in the unrolled configuration. As shown in FIG. 4A, some of the openings 142a can substantially define a diamond shape, and some other openings 142b can substantially define a conjoined series of diamond and partial-diamond shapes. As shown, in the unrolled configuration, the stent spring 120 can be substantially flat and can define a first end 450 and an opposing second end 452. According to example aspects, the mesh structure of the stent spring 120 can be manufactured in the unrolled configuration, for example, by laser cutting or sterolithography. The stent spring 120 can then be rolled into the rolled configuration. To retain the stent spring 120 in the rolled configuration, the first end 450 of the stent spring 120 can be spot welded, riveted, or otherwise attached by any suitable attachment method, to the second end 452. In other aspects, the first end 450 of the stent spring 120 can be attached to the second end 452 by a fastener, such as, for example, one or more nut and bolt assemblies, adhesives, clips, snaps, ties, or any other suitable fastener or combination of fasteners know in the art. Furthermore, according to example aspects, the rolled stent spring 120 (or in other aspects, the unrolled stent spring 120) can be heat treated to harden the stent spring 120. In one example aspect, the stent spring 120 can be hardened to between about 40-45 HRC, for example and without limitation circular.

Figure 5A:
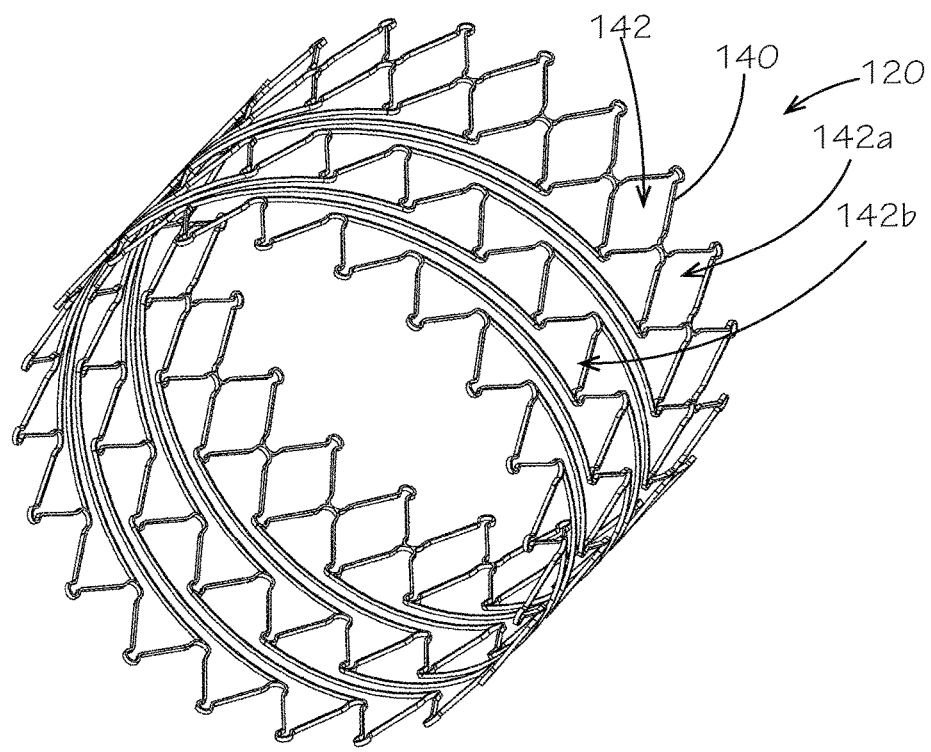
FIG. 5A is a bottom perspective view of the stent spring, in accordance with another aspect of the present disclosure, in the rolled configuration.
Figure 5B:
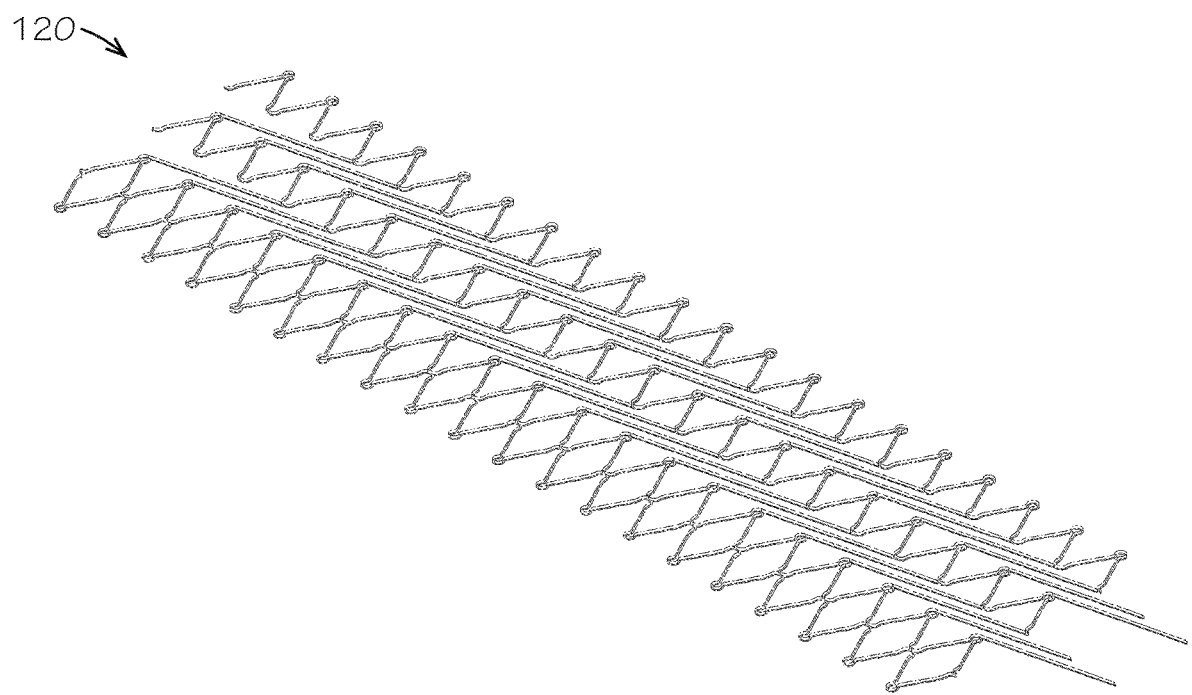
FIG. 5B is perspective view of the stent spring of FIG. 5A in the unrolled configuration.
Figure 6A:
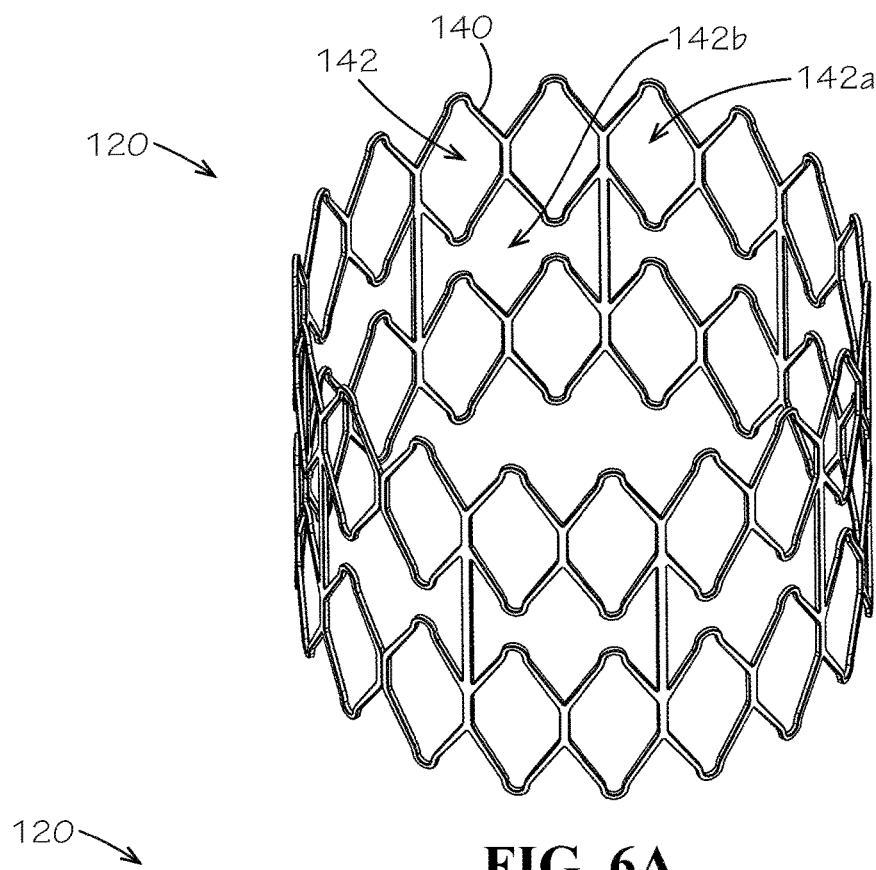
FIG. 6A is a top perspective view of the stent spring, in accordance with another aspect of the present disclosure, in the rolled configuration.
Figure 6B:
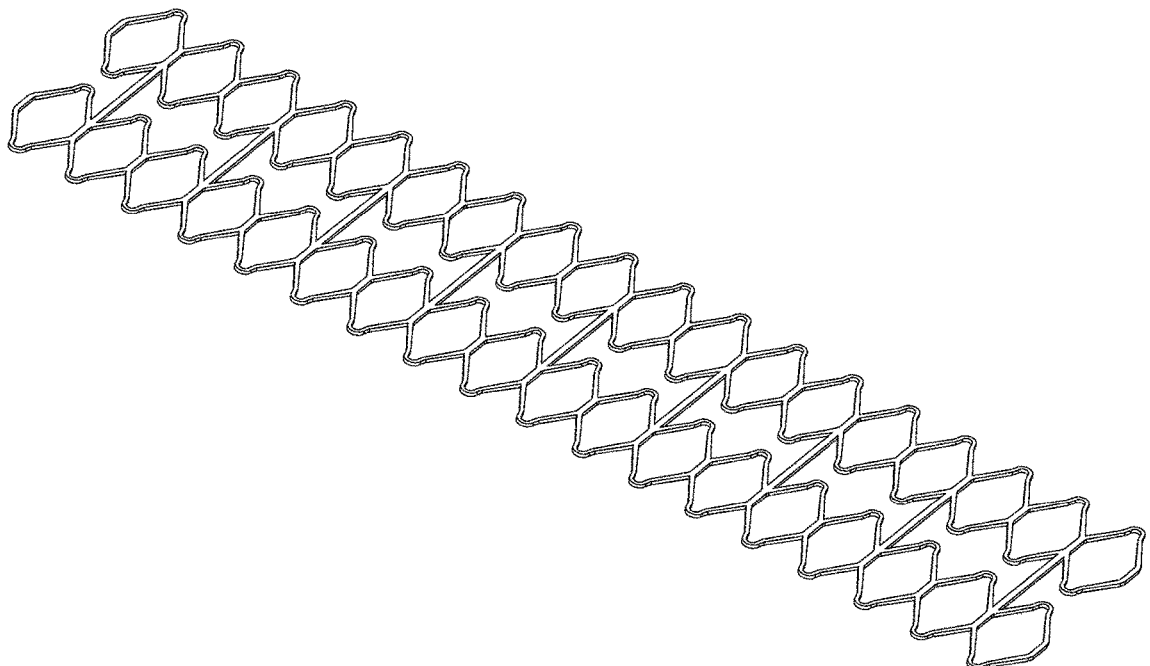
FIG. 6B is perspective view of the stent spring of FIG. 6A in the unrolled configuration.
Figure 7A:
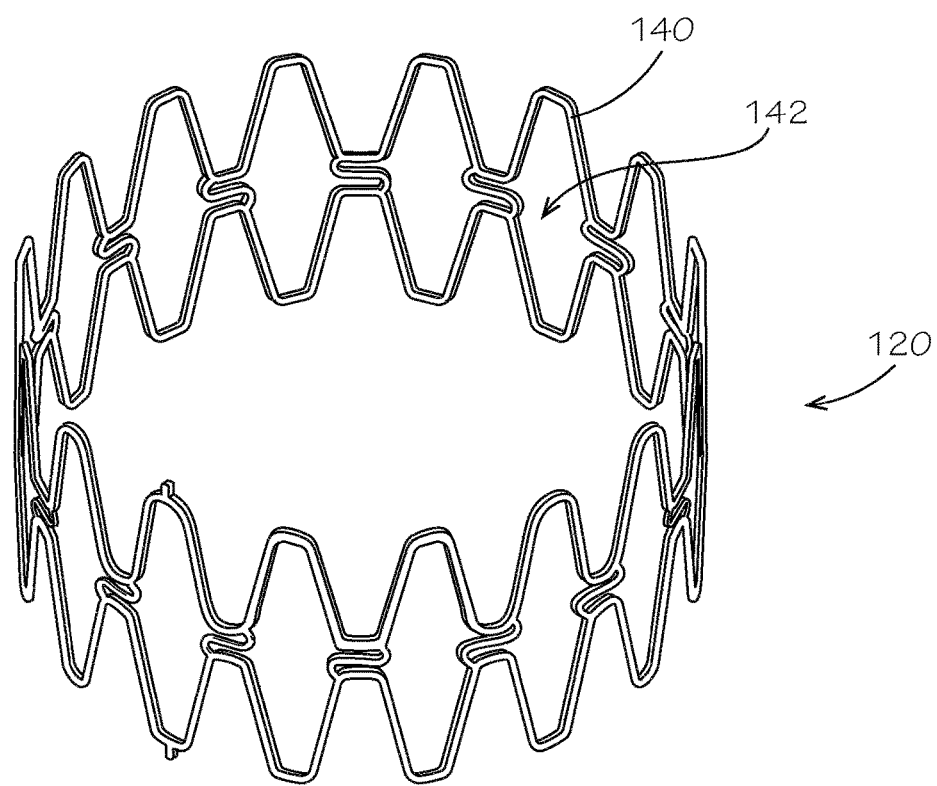
FIG. 7A is a top perspective view of the stent spring, in accordance with another aspect of the present disclosure, in the rolled configuration.
Figure 7B:
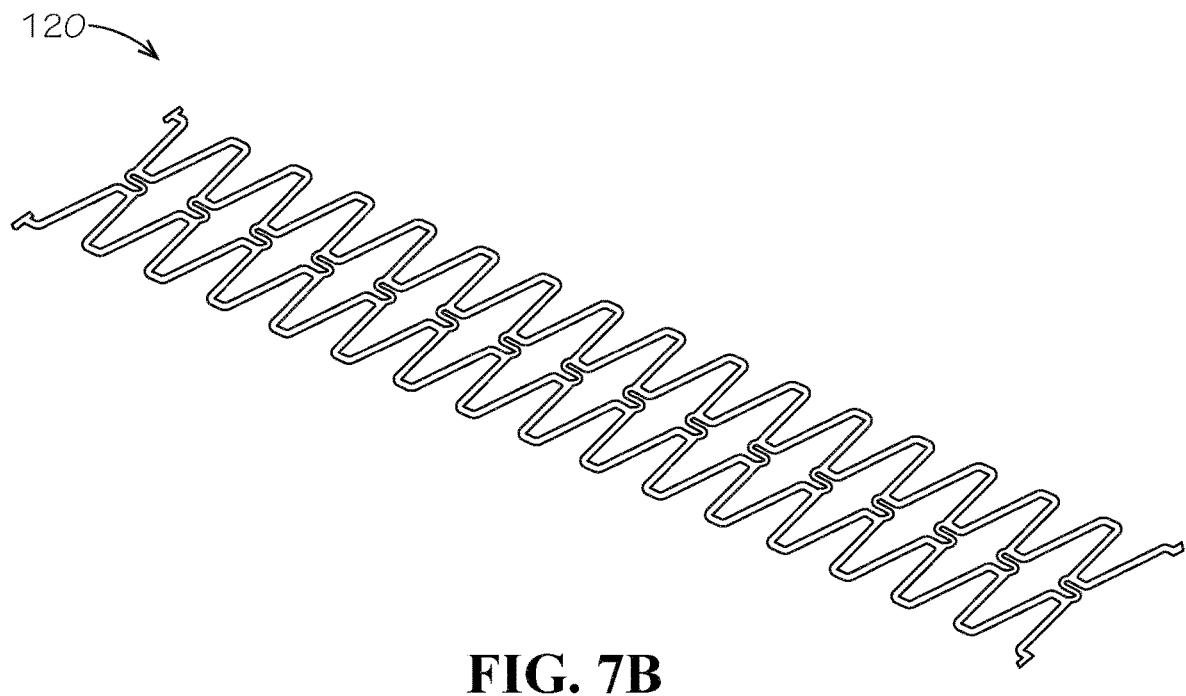
FIG. 7B is perspective view of the stent spring of FIG. 7A in the unrolled configuration.
Figure 8A:
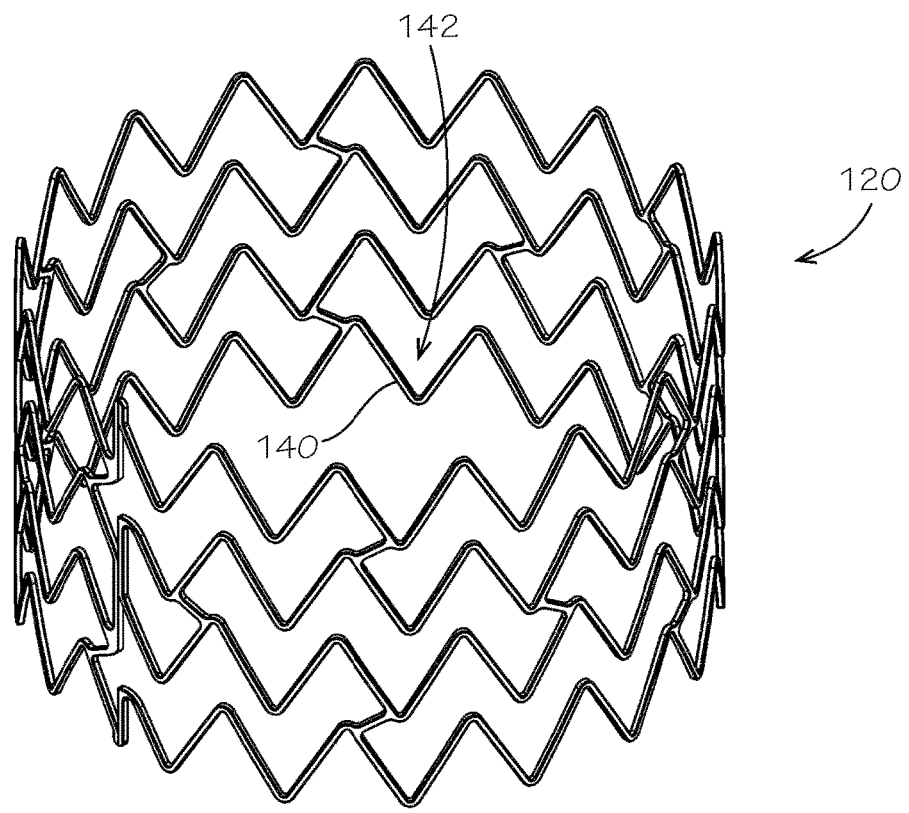
FIG. 8A is a top perspective view of the stent spring, in accordance with another aspect of the present disclosure, in the rolled configuration.
Figure 8B:
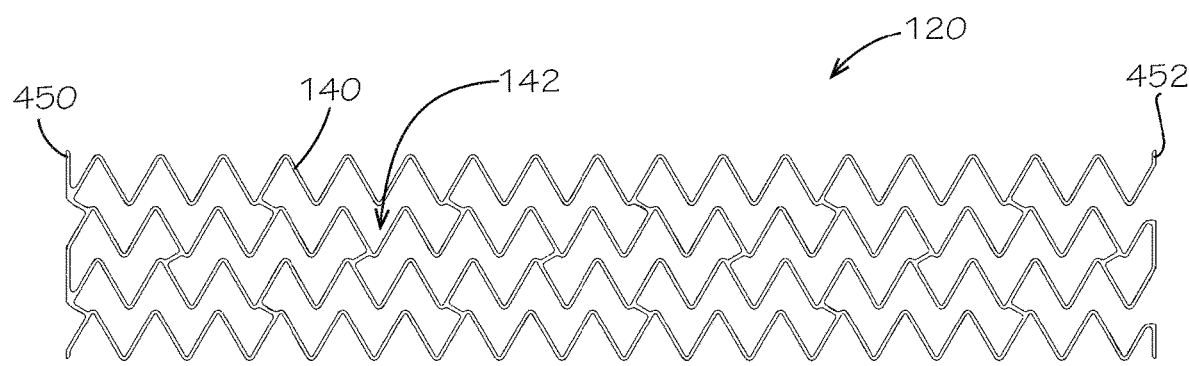
FIG. 8B is front view of the stent spring of FIG. 8A in the unrolled configuration.

FIG. 5A illustrates the stent spring 120 in the rolled configuration, according to another aspect of the present disclosure, and FIG. 5B illustrates the stent spring 120 of FIG. 5A in the unrolled configuration. Referring to FIG. 5A, in the present aspect, some of the openings 142a can substantially define a diamond shape, and some other openings 142b can substantially define a pair of half-diamond shapes connected by an elongated rectangular shape. FIG. 6A illustrates the stent spring 120 in the rolled configuration, according to yet another aspect of the present disclosure, and FIG. 6B illustrates the stent spring 120 of FIG. 6A in the unrolled configuration. Referring to FIG. 6A, in the present aspect, some of the openings 142a can substantially define a diamond shape, and some other openings 142b can substantially define a series of diamond and half-diamond shapes. FIG. 7A illustrates still another aspect of the stent spring 120 in the rolled configuration, and FIG. 7B illustrates the stent spring 120 of FIG. 7A in the unrolled configuration. In the present aspect, the openings 142 can substantially define an elongated hexagonal shape. FIG. 8A illustrates the stent spring 120 in the rolled configuration, according to a further aspect of the present disclosure, and FIG. 8B illustrates the stent spring 120 of FIG. 8A in the unrolled configuration. In the present aspect, the openings 142 can substantially define a chevron pattern.

Figure 9A:
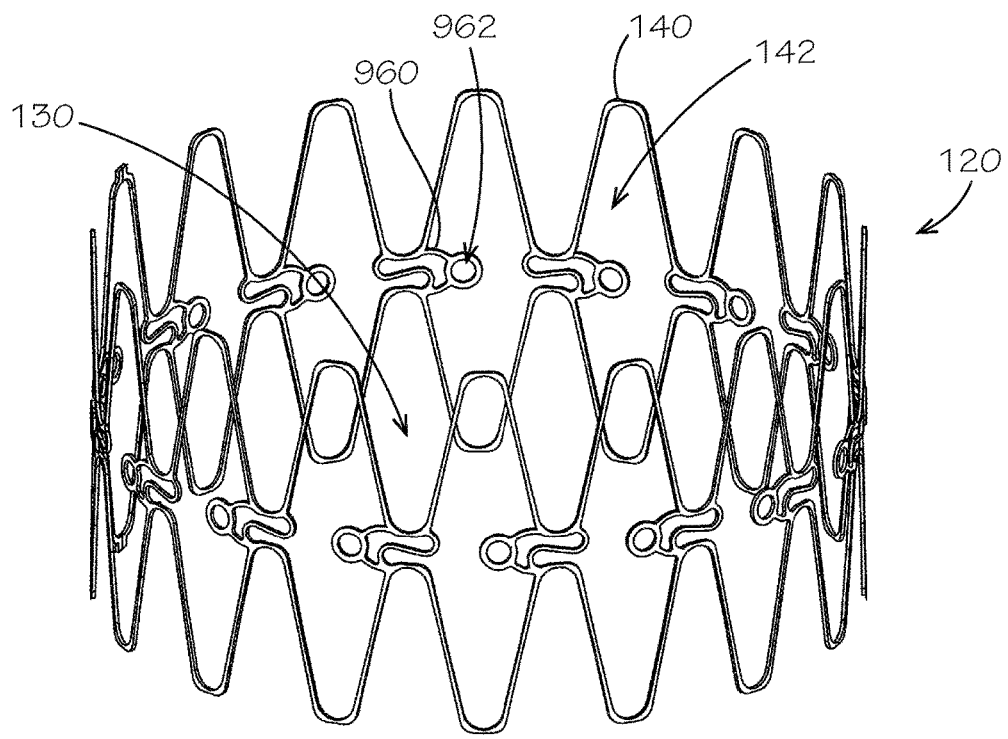
FIG. 9A is a top perspective view of the stent spring, in accordance with another aspect of the present disclosure, in the rolled configuration.
Figure 9B:
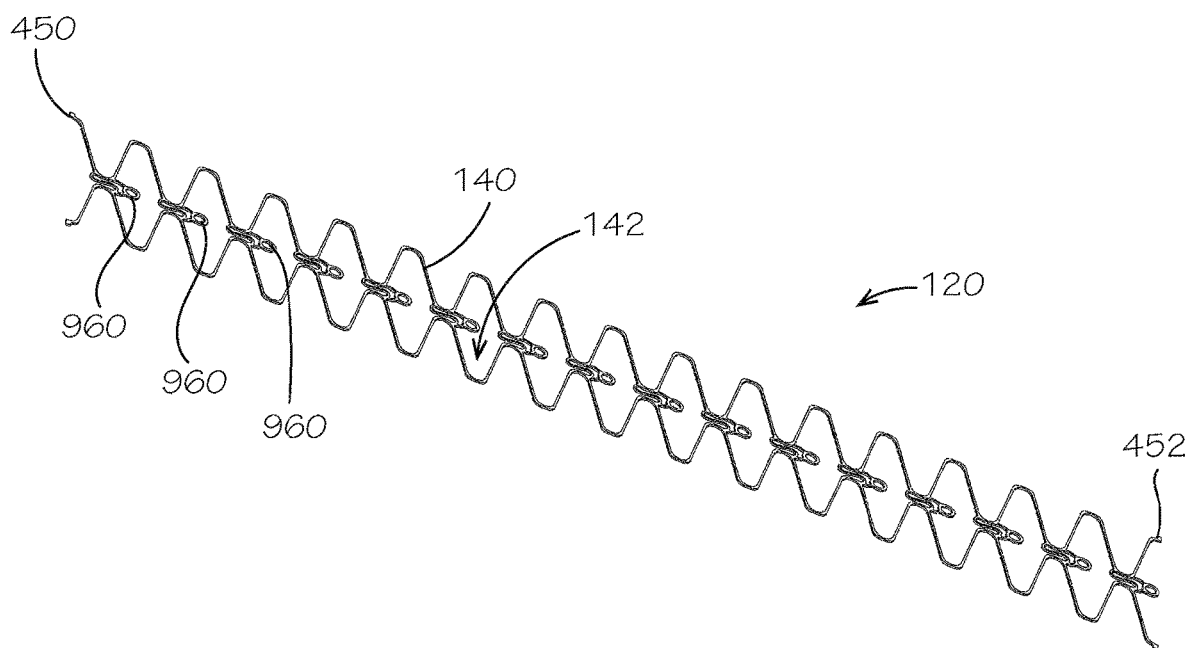
FIG. 9B is perspective view of the stent spring of FIG. 9A in the unrolled configuration.

FIG. 9A illustrates the stent spring 120 in the rolled configuration, according to yet another aspect of the present disclosure, and FIG. 9B illustrates the stent spring 120 of FIG. 9A in the unrolled configuration. In the present aspect, the openings 142 can substantially define an elongated hexagonal shape. Furthermore, in the present aspect, the stent spring 120 can comprise a spring steel material. Example aspects can be coated with a rubber or liquid metal material, zinc-nickel material, phosphate, electrophoretic paint (e-coating), polyester, or fusion-bonded epoxy (FBE), as described above. In other aspects, the stent spring 120 can comprise a stainless steel material, or any other suitable spring material. As shown, example aspects of the stent spring 120 can comprise one or more tabs 960, each defining a tab opening 962 therethrough. The tabs 960 can be bent inward towards the void 130 and the compression mechanism can engage the tabs 960 to compress the stent spring 120 to the compressed stent spring configuration. In a first example aspects, a cable (not shown), or other fastening device, can pass through the tab opening 962 of each of the tabs 960 and can be tightened to contract the stent 100 (shown in FIG. 1A) to the compressed configuration.

Figure 10:
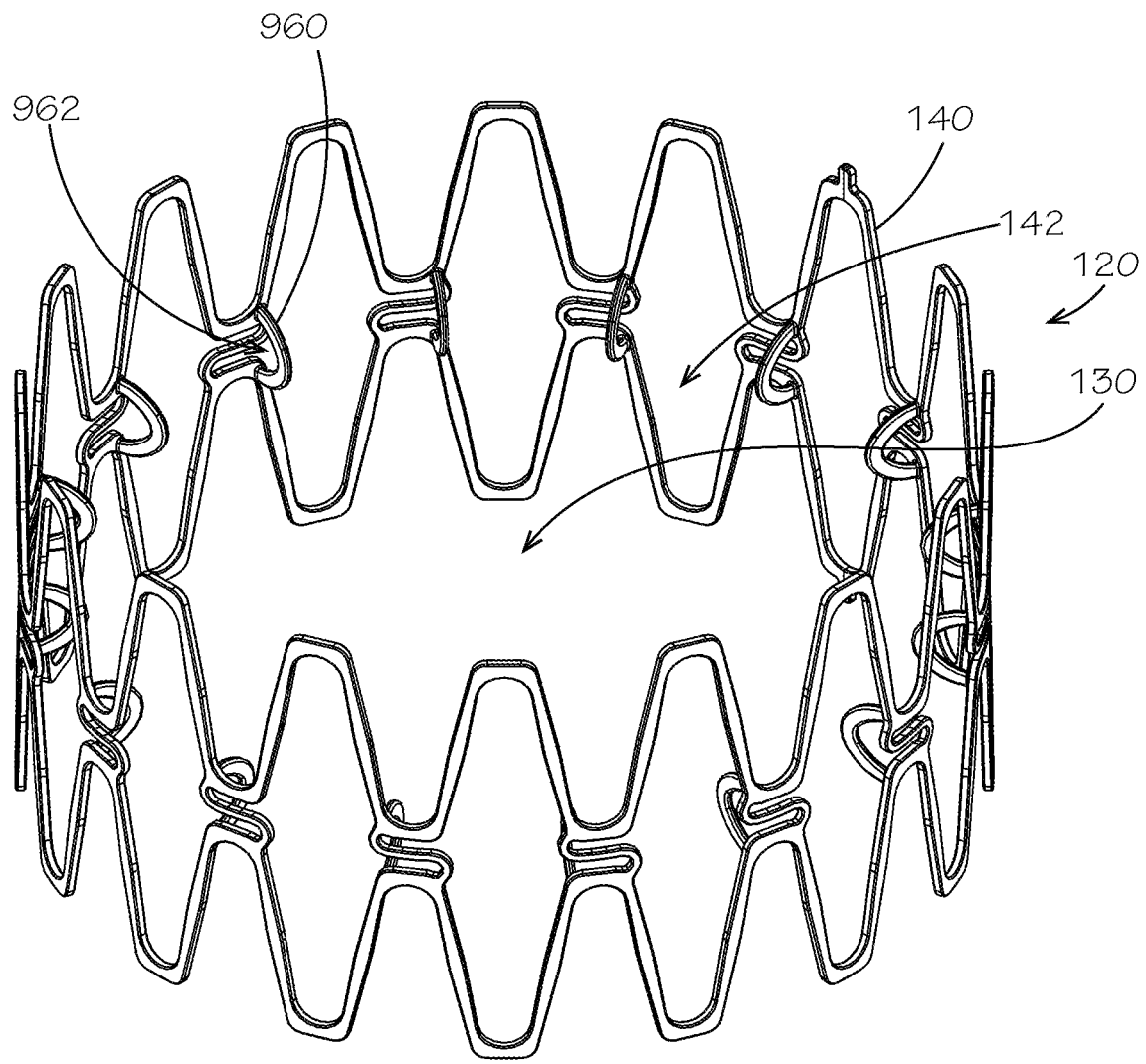
FIG. 10 is a top perspective view of the stent spring, in accordance with another aspect of the present disclosure.

FIG. 10 illustrates still another aspect of the stent spring 120 the rolled configuration. In the present aspect, the openings 142 can substantially define an elongated hexagonal shape. Furthermore, in the present aspect, the stent spring 120 can comprise a carbon fiber material. As shown, the stent spring 120 comprises the tabs 960 extending radially inward towards the void 130. In the present aspect, the tabs 960 can be formed extending inward rather than having to be bent inwards, as may be required by the aspect of FIG. 9A. Each of the tabs 960 can define one of the tab openings 962 therethrough. As described above, in example aspects, a cable (not shown) can pass through the tab opening 962 of each of the tabs 960 and can be tightened to contract the stent 100 (shown in FIG. 1A) to the compressed configuration through tension in the cable. The cable can be cut to release the tension force on the stent 100 and to allow the stent spring 120 to return to the expanded stent spring configuration, thus biasing the stent 100 to the expanded configuration. In other aspects, the stent 100 can be compressed by another compression or contraction mechanism, such as a compression sleeve or tube, a dissolvable wire, or any other suitable mechanisms known in the art. In an aspect comprising a dissolvable wire, the wire can be dissolved by electricity, chemicals, water, or any other suitable dissolving mechanism. In still another aspect, the compression mechanism can be a hose clamp. In some aspects, the hose clamp or other compression mechanism can comprise a worm drive.

Figure 11:
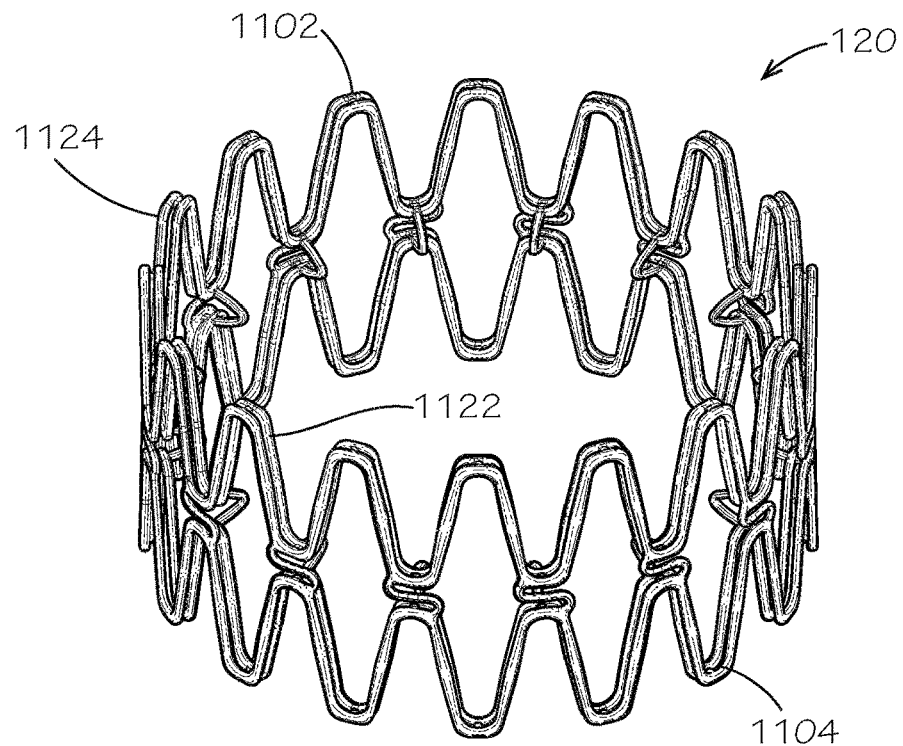
FIG. 11 is a top perspective view of the stent spring, according to another aspect of the present disclosure.

FIG. 11 illustrates another example aspect of the stent spring 120 in the rolled configuration. As shown, the present stent spring 120 can comprise an inner stent spring 1122 aligned and connected with an outer stent spring 1124 to provide increased stiffness of the stent spring 120, while maintaining flexibility of the stent spring 120. Each of the inner stent spring 1122 and outer stent spring 1124 of the present aspect can be substantially similar in shape to the stent spring 120 illustrated in FIG. 10; however, in other aspects, the inner and outer stent springs 1122,1124 can be differently shaped. In one example aspect, the inner and outer stent springs 1122,1124 can be formed from carbon fiber, and in another example aspect, the inner and outer stent springs 1122,1124 can be formed from nylon. In other aspects, the inner and outer stent springs 1122,1124 can be formed from any suitable material, including but not limited to stainless steel, spring steel, aluminum, nitinol, cobalt chromium, POM (polyoxymethylene), and PVC (polyvinyl chloride). According to example aspects, the inner and outer stent springs can be joined together at a plurality of upper bends 1102 and lower bends 1104 thereof, as shown.

Figure 12:
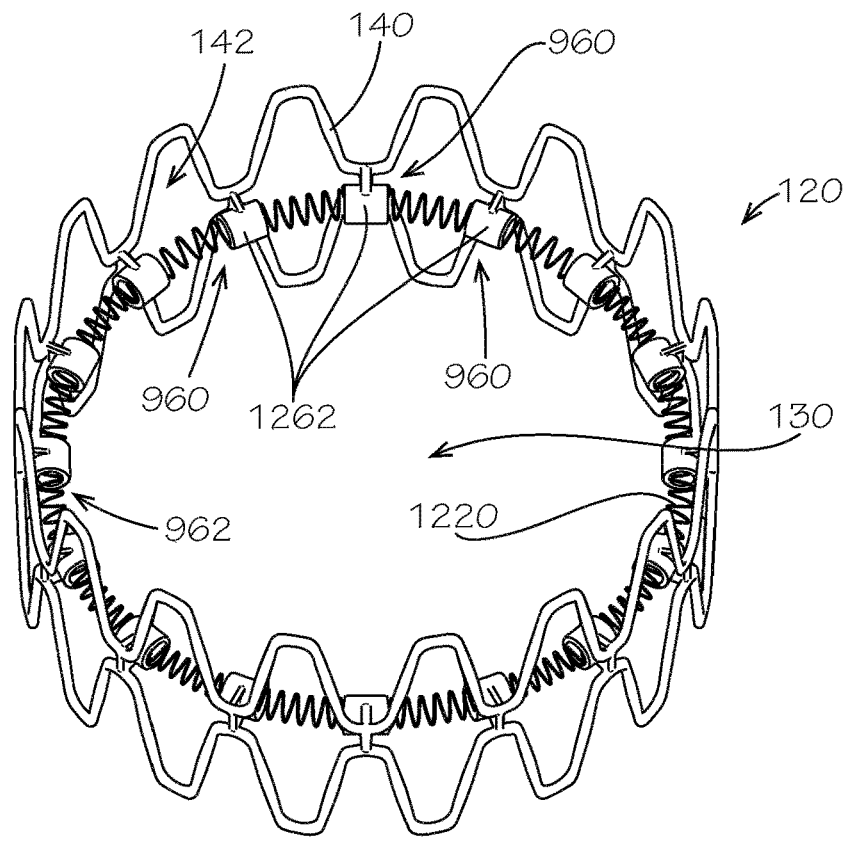
FIG. 12 is a top perspective view of the stent spring in the rolled configuration, according to another aspect of the present disclosure.
Figure 13:
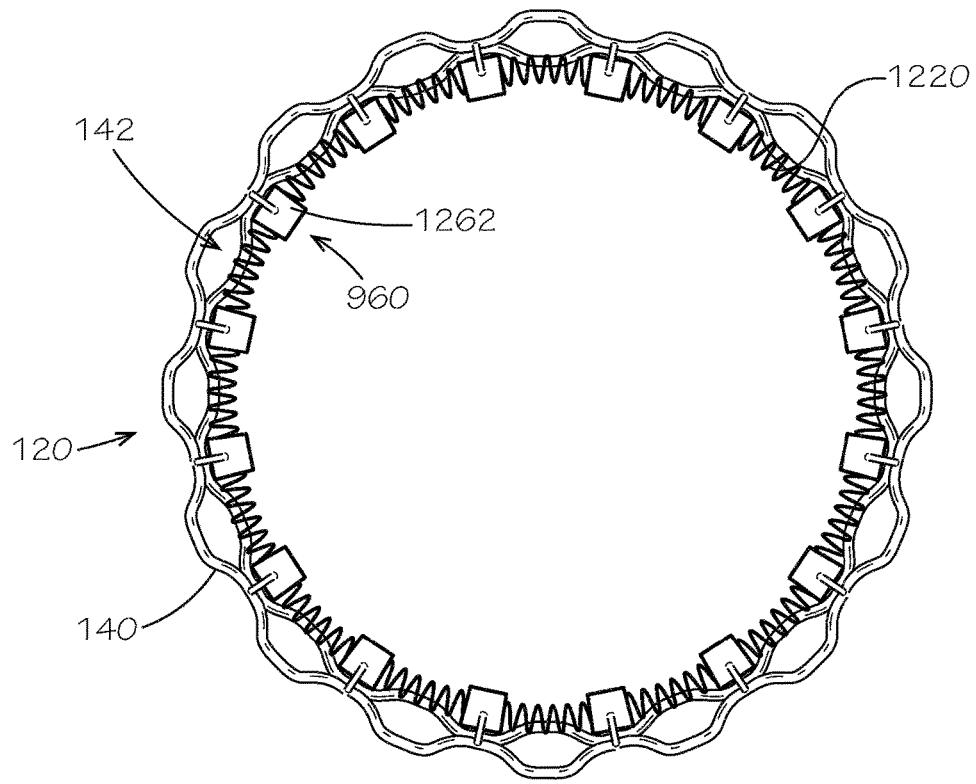
FIG. 13 is a top view of the stent spring of FIG. 12.
Figure 14:
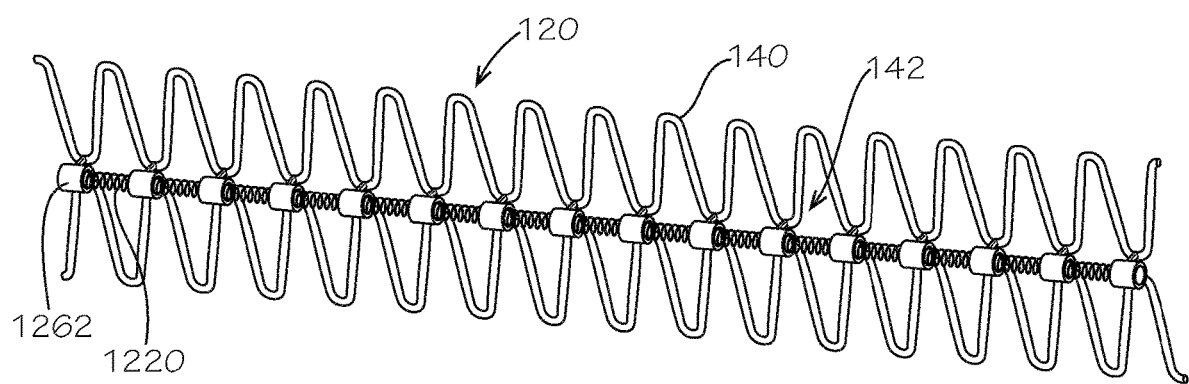
FIG. 14 is a perspective view of the stent spring of FIG. 12 in the unrolled configuration.

FIGS. 12 and 13 illustrates an example aspect of the stent spring 120 in the rolled configuration, wherein the tabs 960 are formed as hollow cylindrical structures 1262 each defining the tab opening 962 extending therethrough. In the present aspect, a coil spring 1220 can extend through the tab openings 962, as shown. The coil spring 1220 can define a coil spring force. In example aspects, like the stent spring 120, the coil spring 1220 can be compressed in the compressed stent spring configuration and can be expanded in the expanded stent spring configuration. As described above, in the compressed stent spring configuration, a compression force (e.g. a pushing force, tension or pulling force, or any other suitable force) can be applied to the stent 100 (shown in FIG. 1A). The compression force can overcome the spring force of the stent spring 120 and the coil spring force of the coil spring 1220, and the stent spring 120, coil spring 1220, and seal 170 (shown in FIG. 1A) can be compressed or folded radially inward towards the void 130. When compressed, the stent 100 can define a smaller stent diameter $D_1$ (shown in FIG. 1A) and a smaller overall stent volume than in the expanded configuration. When the compression force is removed or reduced to less than the spring force and coil spring force, both of the stent spring 120 and the coil spring 1220 can assist in biasing the stent 100 fully back to the expanded configuration. As such, in instances where one of the stent spring 120 and coil spring 1220 may not bias the stent 100 fully back to the expanded configuration on its own, the other of the stent spring 120 and coil spring 1220 can assist in further biasing the stent 100 towards the expanded configuration. Moreover, as shown in FIG. 13, example aspects of the stent spring 120 can be formed from a Windform® material, such as, for example, a Windform® SP material. The Windform SP material is a carbon fiber reinforced composite polyamide material, which can be durable, insulating, and water resistant. FIG. 14 illustrates the stent spring 120 of FIGS. 12 and 13 in the unrolled configuration.

Figure 15:
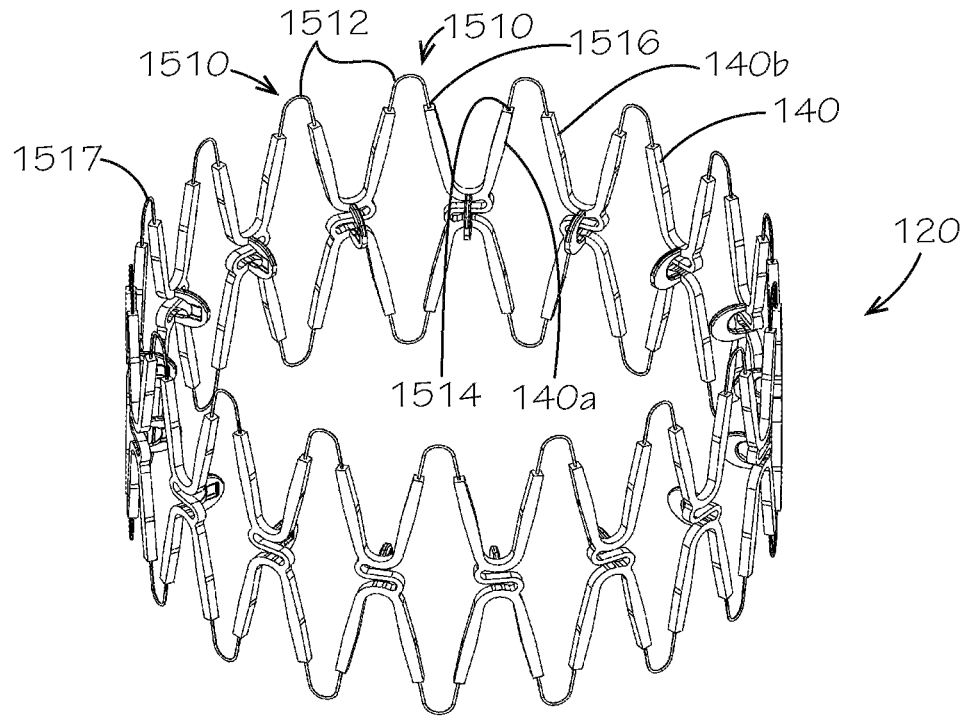
FIG. 15 is a top perspective view of the stent spring, according to another aspect of the present disclosure, wherein the stent spring comprises elastic wires.
Figure 16:
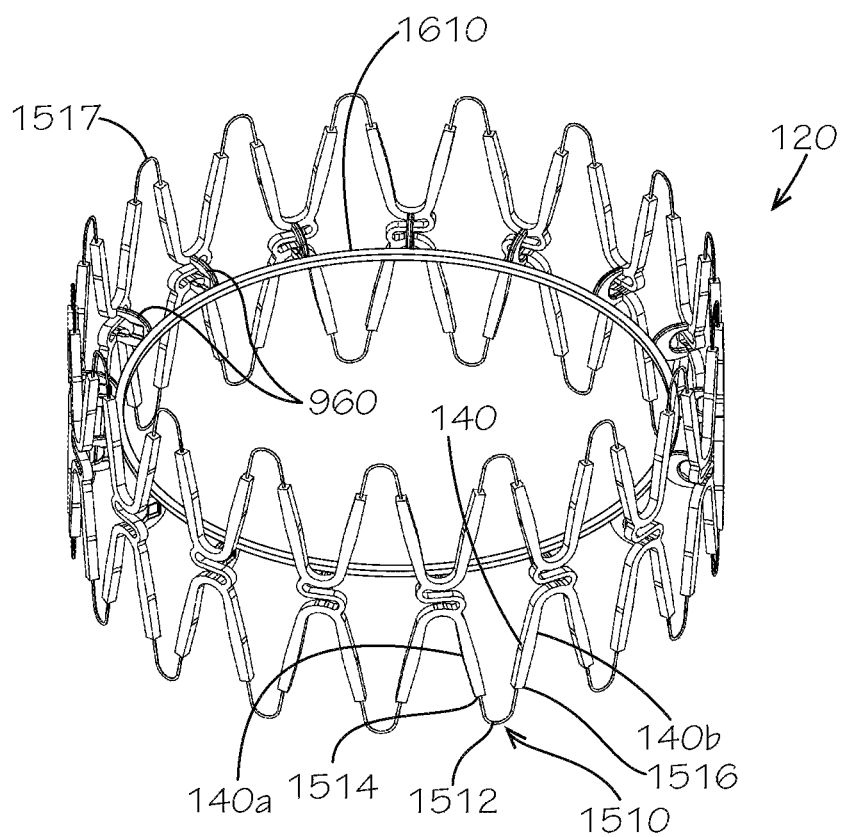
FIG. 16 is a top perspective view of the stent spring of FIG. 15 further comprising a connecting band.

FIGS. 15 and 16 illustrates an example aspect of the stent spring 120 in the rolled configuration, according to another aspect of the present disclosure. The stent spring 120 can be similar to the stent spring 120 illustrated FIG. 10. However, as shown, the stent spring 120 of the present aspect can further comprise a wire or wires 1510 connected to one or more of the strands 140 of the stent spring 120. In one example aspect, the wires 1510 can be a plurality of Nitinol super-elastic wires 1512, which can be configured to provide added flexibility to the stent spring 120. In example aspects, each of the Nitinol super-elastic wires 1512 can define a first end 1514, a second end 1516, and a middle section 1517 extending therebetween. The first end 1514 can be received within a first groove (not shown) formed within a corresponding first strand 140*a*, and the second end 1516 can be received within a second groove (not shown) of an adjacent second strand 140*b*.

Figure 17:
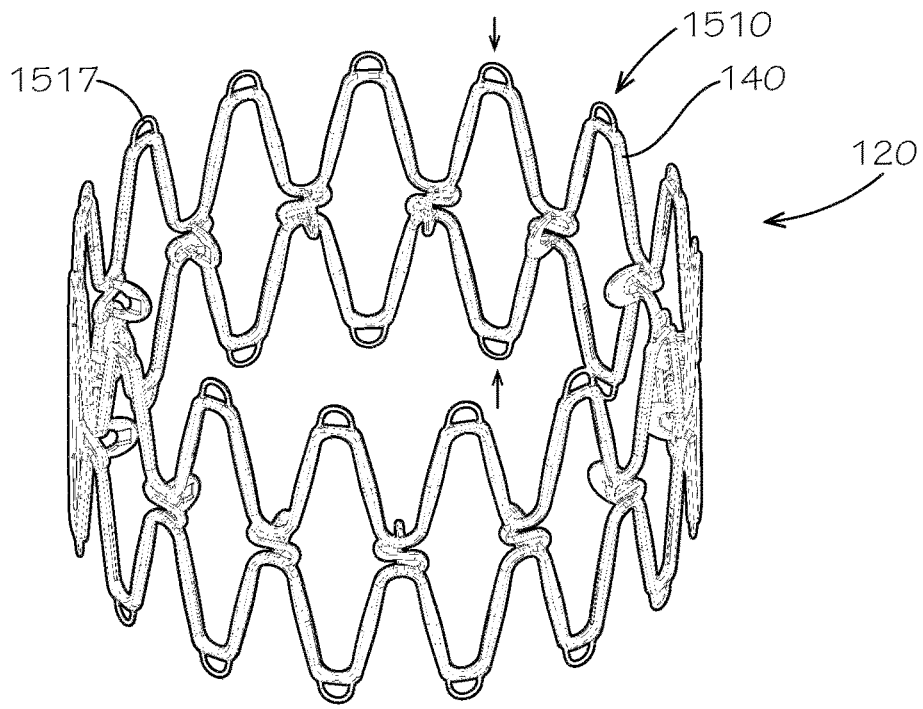
FIG. 17 is a top perspective view of another aspect of the stent spring comprising the elastic wires.
Figure 18:
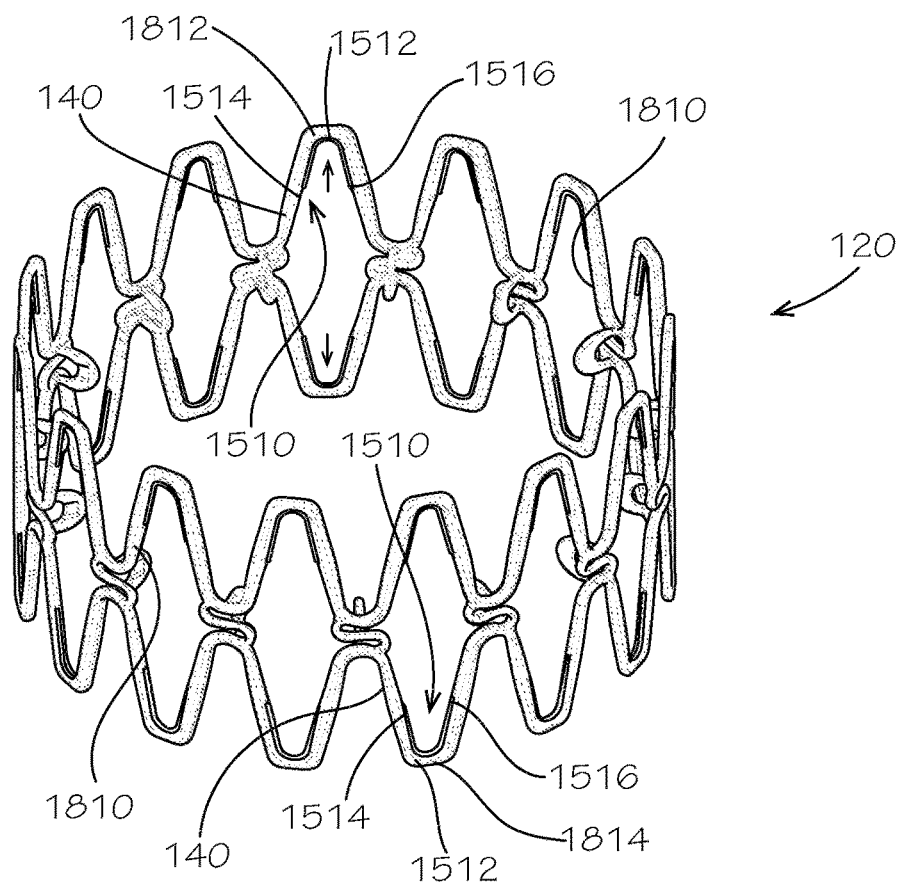
FIG. 18 is a top perspective view of another aspect of the stent spring comprising the elastic wires.
Figure 19:
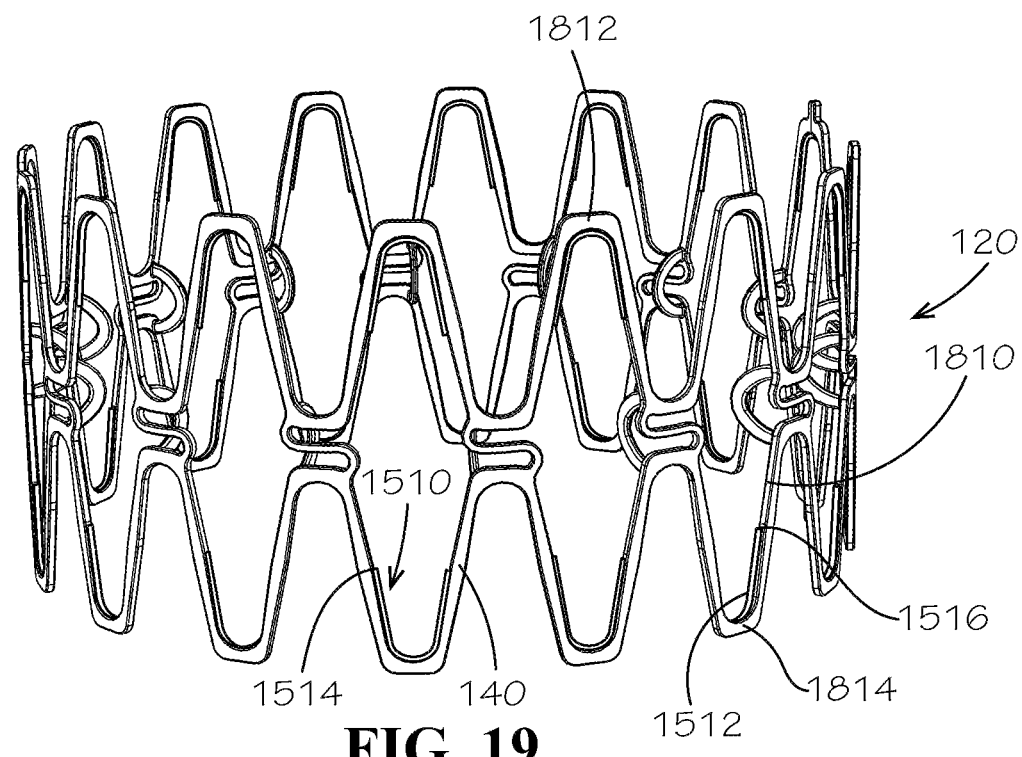
FIG. 19 is a top perspective view of the stent spring of FIG. 18.

As shown in FIG. 16, in some aspects, the compression mechanism can be a connecting band 1610. The connecting band 1610 can engage each of the tabs 960 of the stent spring 120 to retain the stent spring 120 in the compressed stent spring configuration while the wires 1510 are assembled with the stent spring 120. Furthermore, in the present aspect, the middle section 1517 of each wire 1510 can be substantially exposed. However, in other aspects, the wires 1510 can be more fully received within the strands 140 of the stent spring 120, such that a lesser portion of the middle section 1517 is exposed, as depicted in FIG. 17, and in still other aspects, the wires 1510 can be completely received within the strands 140. FIGS. 18 and 19 illustrates another aspect, wherein each of the wires 1510 can be positioned on an inner periphery 1810 of the stent spring 120 proximate to an upper bend 1812 or lower bend 1814 thereof. In one aspect, the wires 1510 can be connected to the stent spring 120 by an adhesive, or other fastener, and the first and second ends 1514,1516 of the wires 1510 do not extend into the strands 140. However, in other aspects, the first and second ends 1514,1516 of each of the wires 1510 can engage the first and second grooves (not shown) formed in a corresponding strand 140 to connect the wire 1510 to the stent spring 120.

Figure 20:
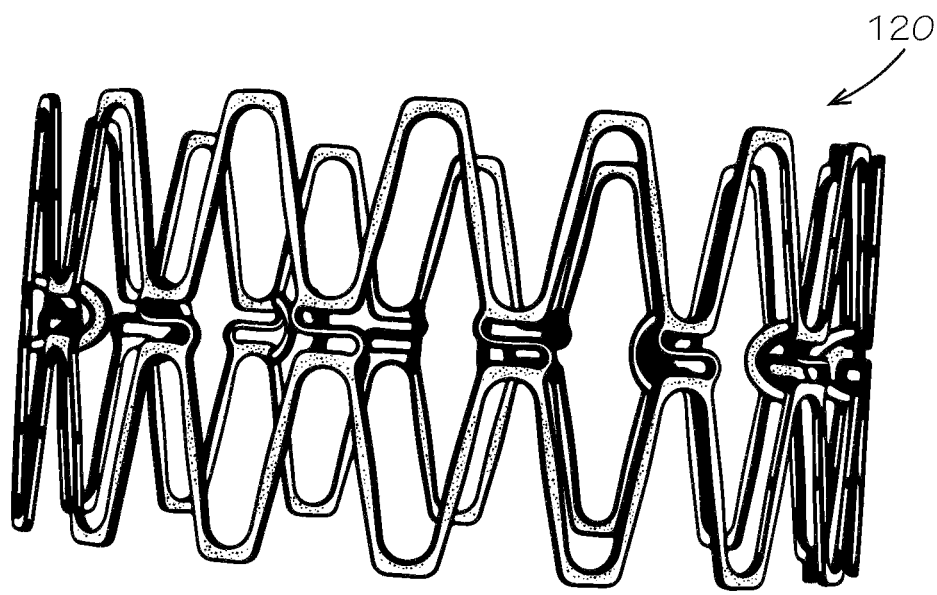
FIG. 20 is a front view of the stent spring comprising a rubber coating according to another aspect of the present disclosure.
Figure 21:
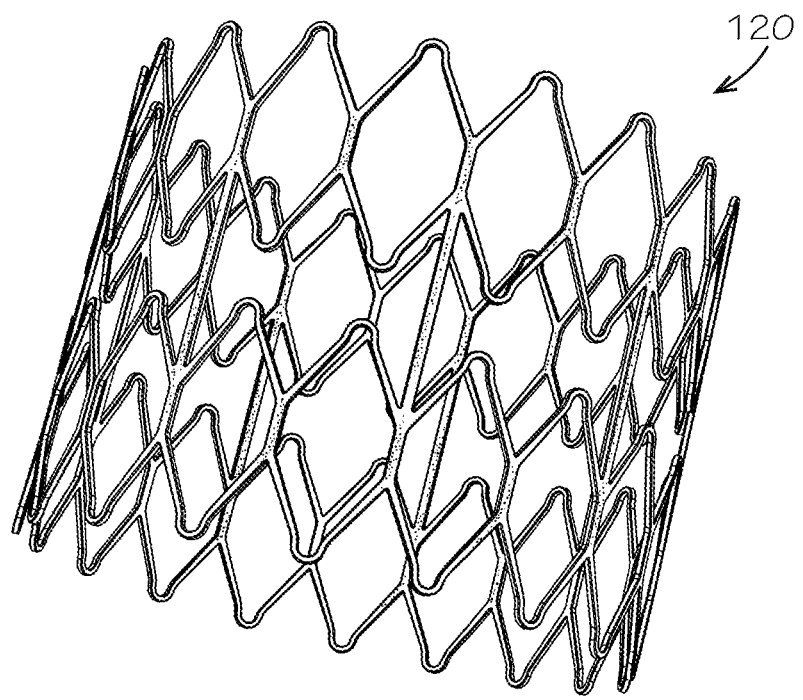
FIG. 21 is a perspective view of the stent spring comprising the rubber coating according to another aspect of the present disclosure.
Figure 22:
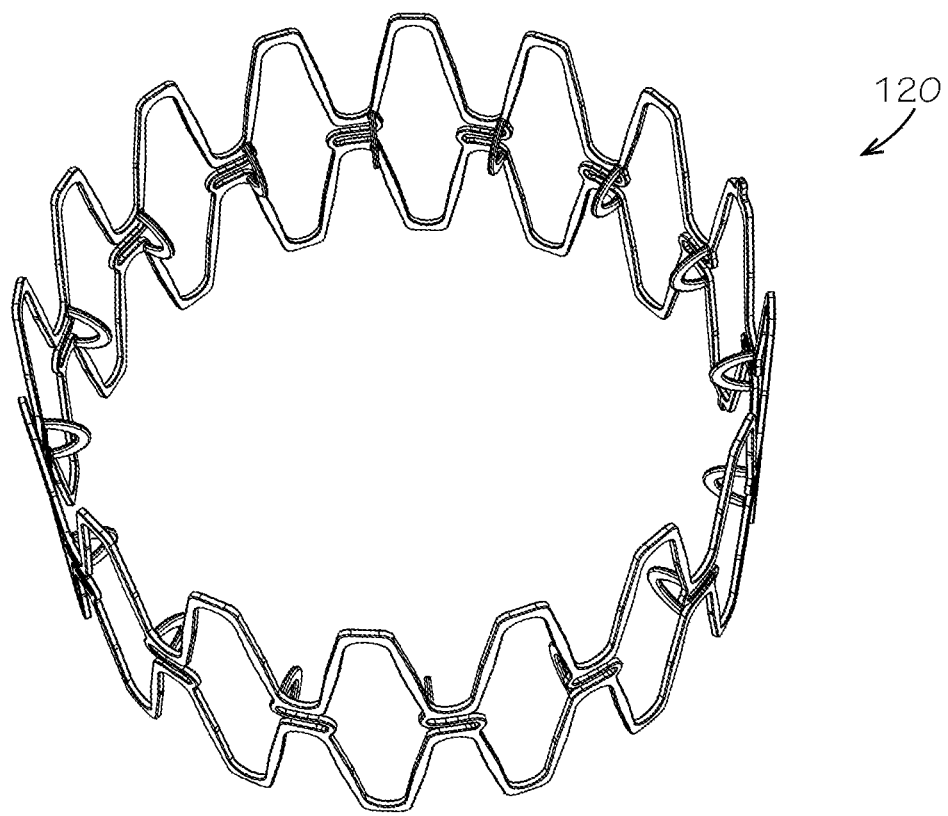
FIG. 22 is a top perspective view of the stent spring of FIG. 20 without the rubber coating.

Example aspects of the stent spring 120 can comprise a coating, such as, for example, a rubber coating. For example, as shown in the aspect of FIG. 20, the stent spring 120 can be coated in a Plasti Dip® coating. A Plasti Dip® coating is a synthetic rubber coating that can be applied by spraying, brushing, dipping, or the like, and which can be configured to air dry. The Plasti Dip® material can be non-slip, flexible, durable, and insulating material in some aspects. In another example aspect, as shown in FIG. 21, the stent spring 120 can be coated in a Flex Seal® coating. The Flex Seal® coating is a synthetic rubber coating similar to the Plasti Dip® coating. The Flex Seal® coating can be applied by pouring, rolling, dippy, spraying, or the like, and can be durable, flexible, insulating, and water resistant. In other aspects, the coating can be any other suitable coating known in the art. Example aspects of the coating can be flexible and can improve the flexibility of the stent spring 120. In some example aspects, the coating can also be a non-slip coating that can improve the grip of the stent spring 120 on the seal 170 (shown in FIG. 1A), the pipe (not shown), or any other component engaged by the stent spring 120. FIG. 22 illustrates the stent spring 120 of FIG. 20 without the Plasti Dip® coating applied.

Figure 23:
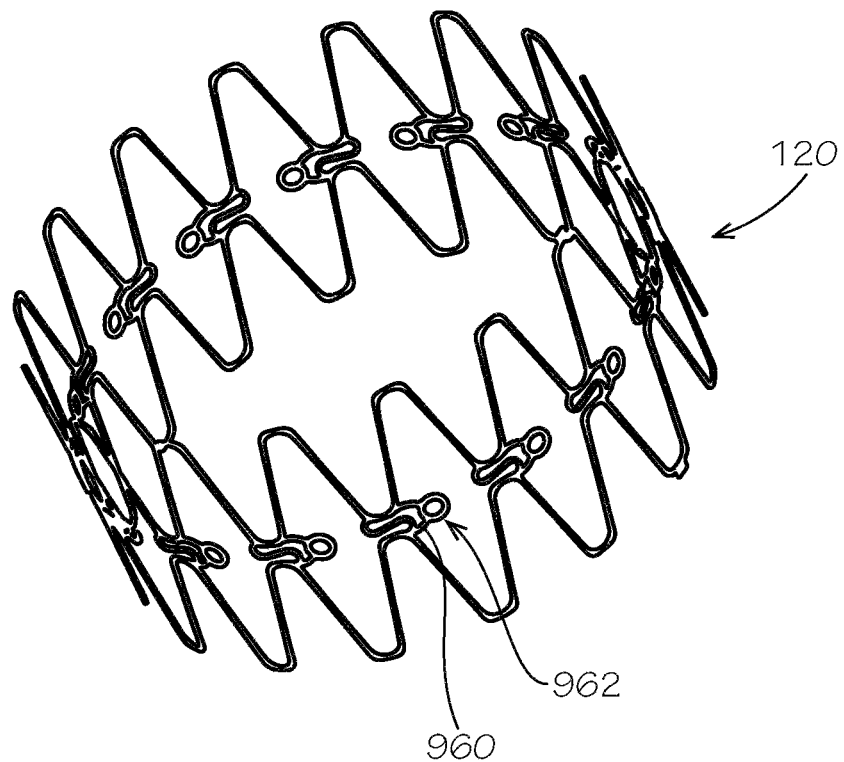
FIG. 23 is a top perspective view of the stent spring in accordance to another aspect of the present disclosure.
Figure 24:
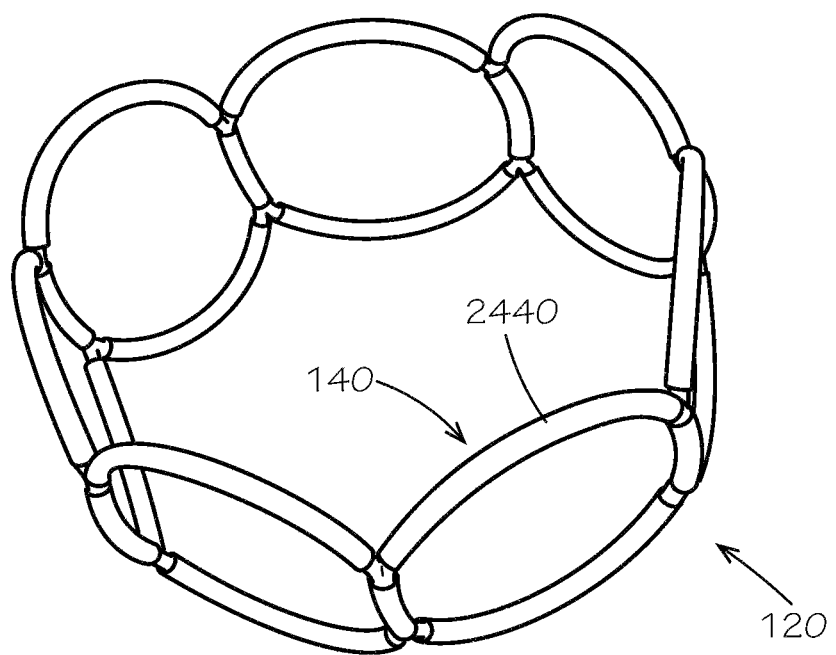
FIG. 24 is a top perspective of another aspect of the stent spring, according to another aspect of the present disclosure.

FIG. 23 illustrates another example aspect of the stent spring 120 that can be substantially similar to the stent spring 120 of FIG. 9A. However, in the present aspect, as shown, the tabs 960 can define larger tab openings 962 than the tab openings 962 shown in FIG. 9A. The larger tab openings 962 can accommodate for a larger or different compression mechanism for compressing the stent 100 (shown in FIG. 1A). FIG. 24 illustrates still another example aspect of the stent spring 120, wherein the strands 140 of the stent spring 120 can be a plurality of connected, substantially circular, resilient and flexible strands 2440, as shown. The flexibility of the strands 140 can allow the stent spring 120 to be compressed to the compressed stent spring configuration, and the resiliency of the strands 140 can bias the stent spring 120 from the compressed stent spring configuration to the expanded stent spring configuration.

According to example aspects, the stent spring 120 can be compressed by the compression mechanism, as described above. For example, in a particular aspect, the compression mechanism can be an internal compression disc 2510 as illustrated in FIG. 25. According to example aspects, the compression disc 2510 can engage each of the tabs 960 of the stent spring 120 to pull the stent spring 120 radially inward and to retain the stent spring 120 in the compressed stent spring configuration. In the present aspect, the compression disc 2510 can comprise an upper disc 2512 and a lower disc 2712 (shown in FIG. 27) connected to the upper disc 2512. Disc openings 2514 can be formed in each of the upper and lower discs 2512,2712 to allow for fluid flow therethrough. Furthermore, one or more disc slots 2516 can be formed at an outer side edge 2518 of the compression disc 2510.

Figure 26:
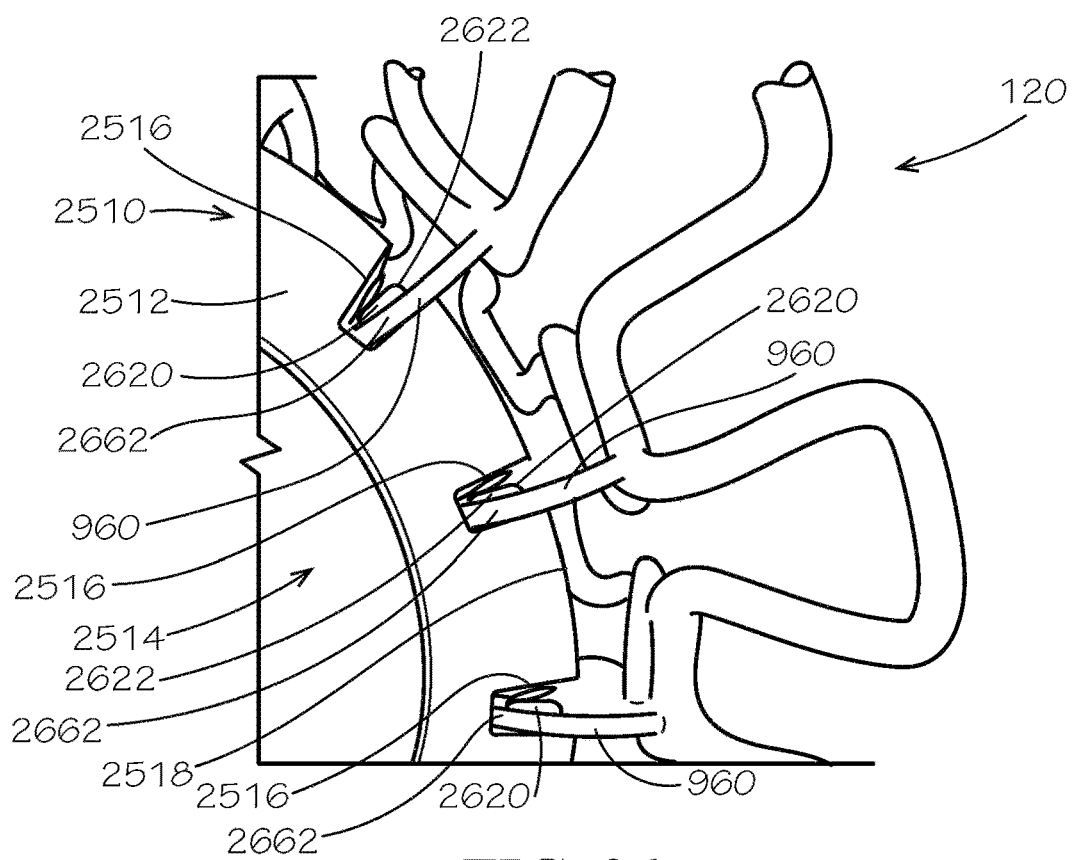
FIG. 26 is a detail view of the stent spring of FIG. 25 retained in the compressed stent spring configuration by the compression mechanism of FIG. 25.
Figure 27:
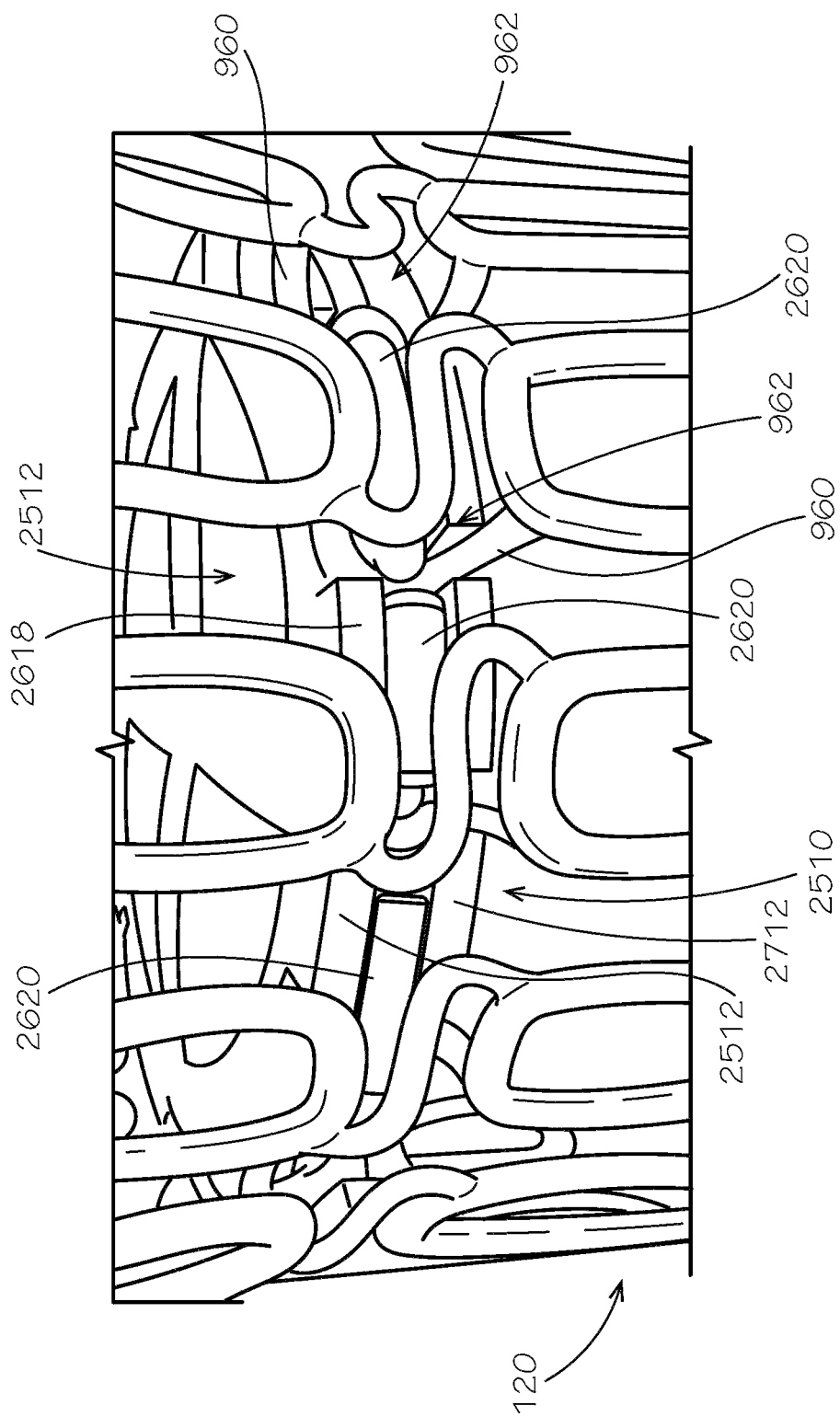
FIG. 27 is another detail view of the stent spring of FIG. 25 retained in the compressed stent spring configuration by the compression mechanism of FIG. 25.

Referring to FIGS. 26 and 27, the compression disc 2510 can further comprise a plurality of connectors 2620 generally received between the upper disc 2512 and lower disc 2712 and proximate to the outer side edge 2518 of the compression disc 2510. A head 2622 of each of the connectors 2620 can be configured to extend into a corresponding one of the disc slots 2516. To mount the stent spring 120 to the compression disc 2510 in the compressed stent spring configuration, an inner end 2662 of each of the tabs 960 can be pushed past the head 2622 of the corresponding connector 2620 and into the corresponding disc slot 2516, such that the head 2622 of each connector 2620 extends through the tab opening 962 (shown in FIG. 9A) of the corresponding tab 960. To move the stent spring 120 to the expanded stent spring configuration, the compression disc 2510 can be slid axially relative to the central axis 132 (shown in FIG. 1A). The tabs 960 of the stent spring 120 can be pushed past the heads 2622 of the corresponding connectors 2620, such that each of the connectors 2620 can be disengaged from the corresponding tab opening 962, and the compression disc 2510 can be disengaged from the stent spring 120. With the compression disc 2510 disengaged from the stent spring 120, the spring force of the stent spring 120 can bias the stent 100 (shown in FIG. 1A) to the expanded configuration.

Figure 28:
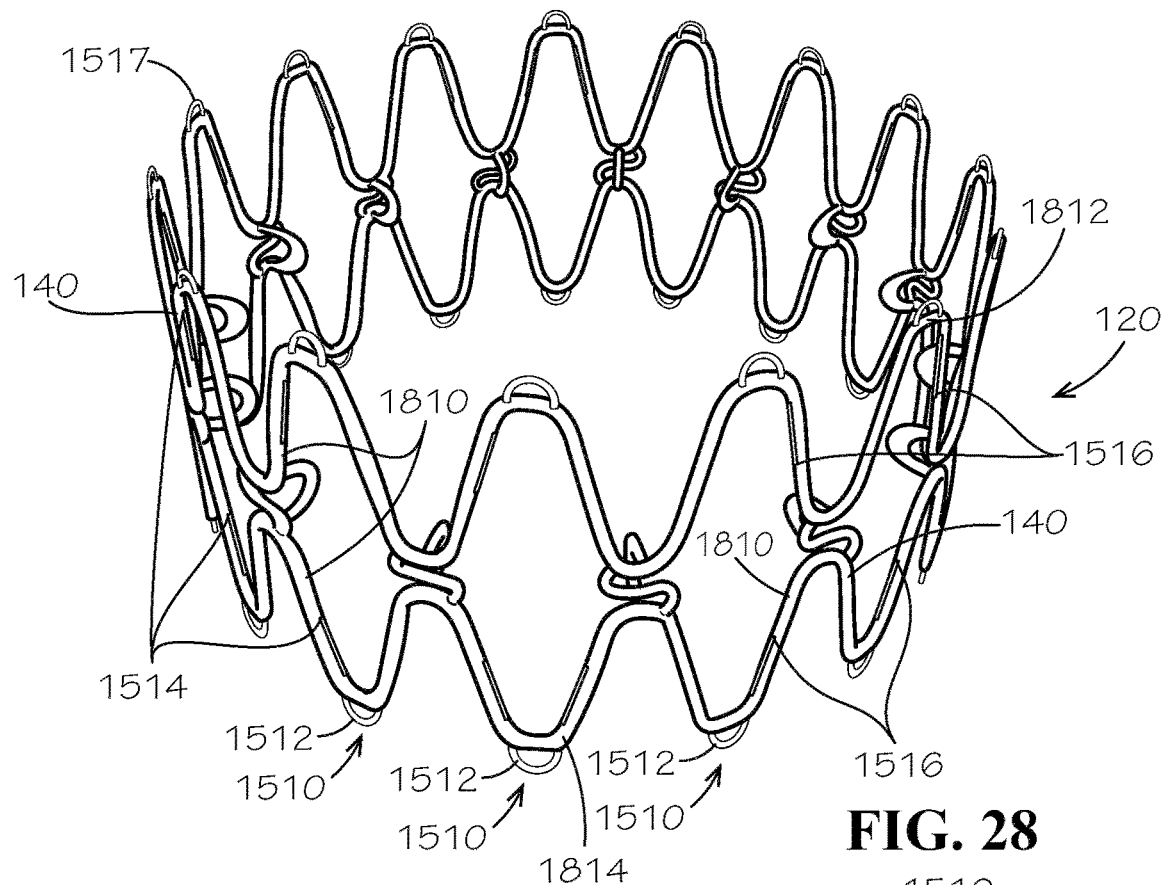
FIG. 28 is a top perspective view of the stent spring comprising the elastic wires, according to another aspect of the present disclosure.
Figure 29:
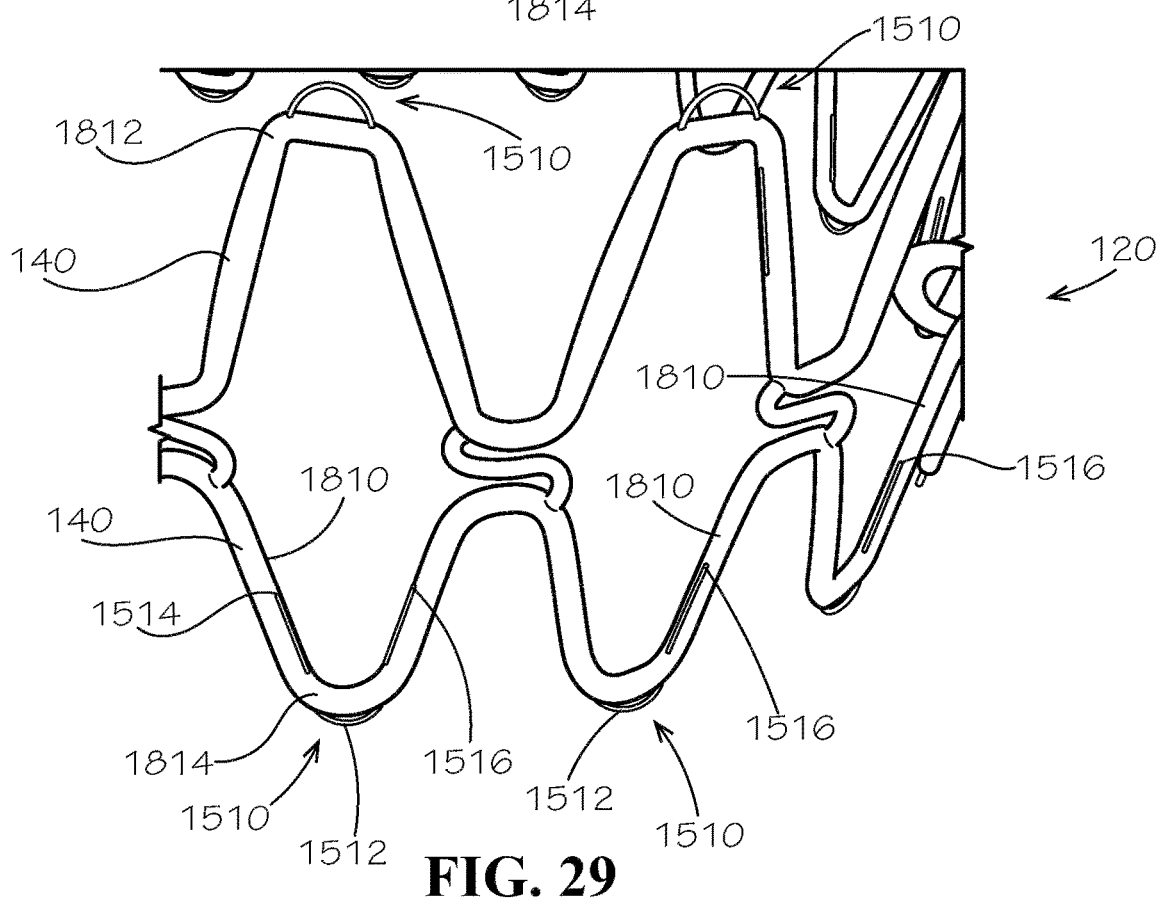
FIG. 29 is a detail view of the stent spring of FIG. 28.

FIGS. 28 and 29 illustrate another aspect of the stent spring 120 comprising the wires 1510 (e.g., the Nitinol super-elastic wires 1512). The stent spring 120 of the present aspect can be similar to the stent spring 120 of FIG. 17, wherein the first end 1514 of each wire 1510 can be received through the first groove (not shown) formed within one of the strands 140, and the second end 1516 of each wire 1510 can be received within the second groove (not shown) formed in the same strand 140. Each wire 1510 can be oriented proximate to one of the upper bends 1812 or lower bends 1814 of the stent spring 120, as shown. In the present aspect, the first and second ends 1514,1516 of each of the wires 1510 can pass through the corresponding first and second grooves, respectively, and can abut the inner periphery 1810 of the stent spring 120 proximate to the corresponding upper or lower bend 1812,1814, as shown. The middle section 1517 can be exposed.

Figure 30:
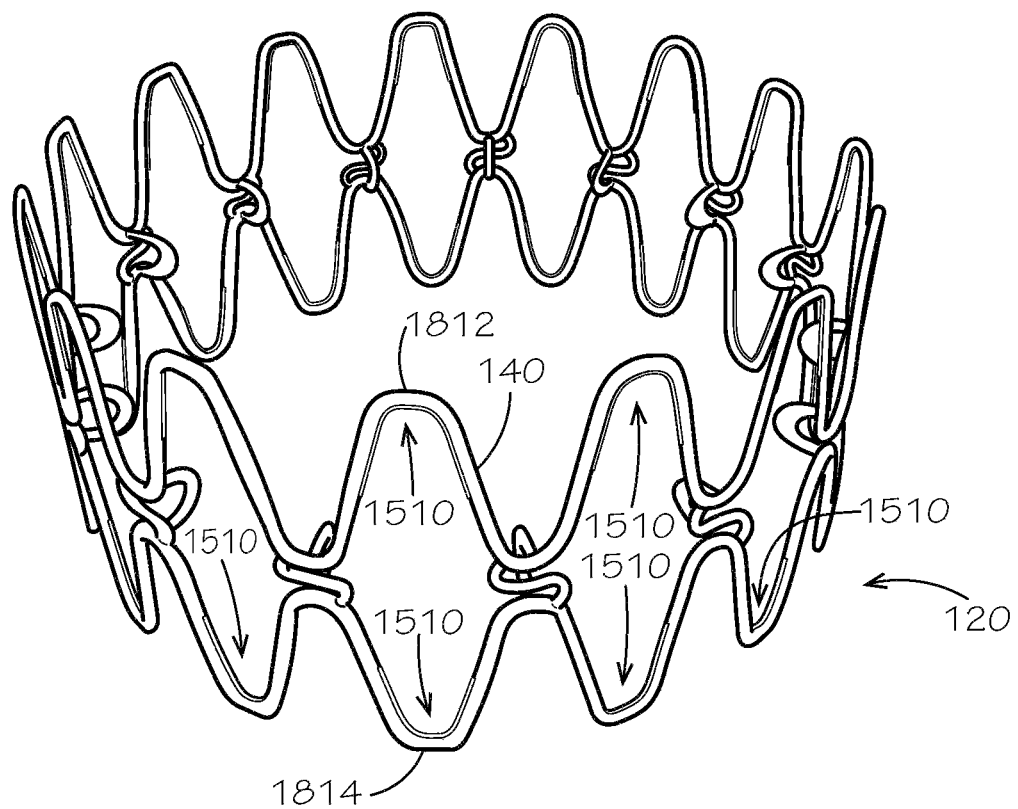
FIG. 30 is a top perspective view of the stent spring of FIG. 18 further comprising the rubber coating.
Figure 31:
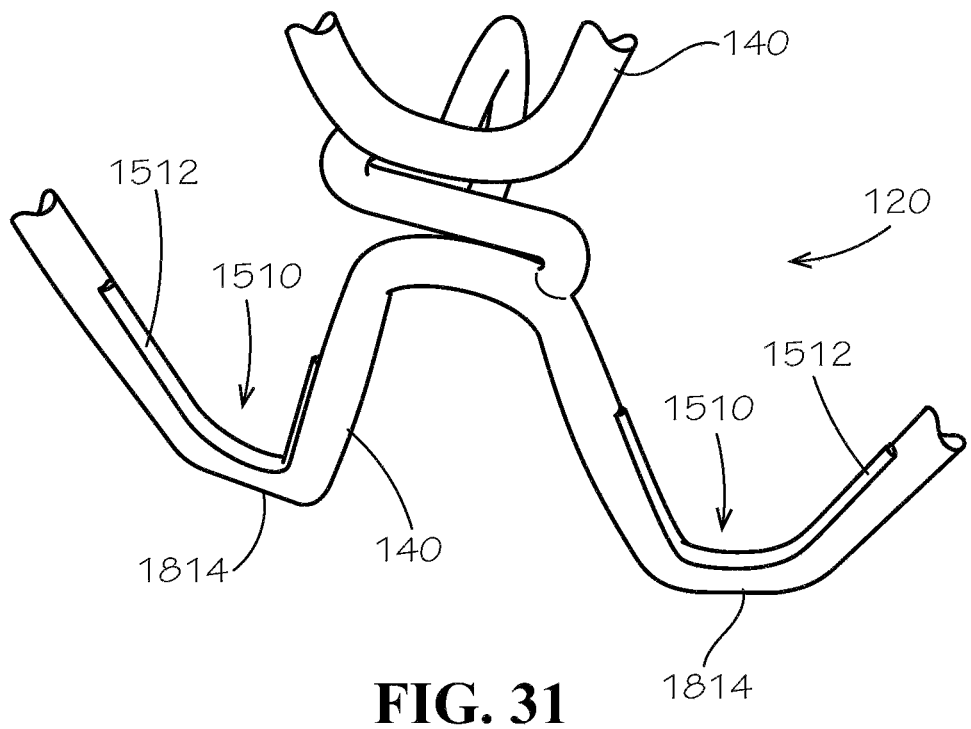
FIG. 31 is a detail view of the stent spring of FIG. 30.

FIGS. 30 and 31 illustrate the stent spring 120 of FIGS. 18 and 19 dipped in the rubber coating, such as, for example, the Plasti Dip® coating or the Flex Seal® coating, as described above with reference to FIGS. 20, 21, and 22.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A stent spring for repairing a pipe comprising:
a substantially tubular mesh structure comprising one or more strands, the one or more strands comprising a spring material, wherein the stent spring is expandable and compressible between an expanded configuration and a compressed configuration; and
an elastic wire connected to the one or more strands, the elastic wire configured to increase a flexibility of the stent spring;
wherein the stent spring further comprises:
a tab extending radially inward from the substantially tubular mesh structure; and
a compression mechanism engaging the tab to retain the stent spring in the compressed configuration.

2. The stent spring of claim 1, wherein;
the elastic wire defines a first end and a second end;
the elastic wire defines a middle section between the first end and second end; and
at least a portion of the middle section is exposed.

3. The stent spring of claim 2, wherein:
the substantially tubular mesh structure defines a first structure end and a second structure end opposite the first structure end; and
the elastic wire extends from the substantially tubular mesh structure at one of the first structure end and the second structure end.

4. The stent spring of claim 3, wherein:
the elastic wire is a first elastic wire of a plurality of elastic wires;
the first elastic wire extends from the substantially tubular mesh structure at the first structure end; and
the plurality of elastic wires further comprises a second elastic wire extending from the second structure end.

5. The stent spring of claim 4, wherein an opening of the stent spring is defined between the first elastic wire and the second elastic wire.

6. The stent spring of claim 4, wherein:
the stent spring defines a void extending from the first structure end to the second structure end; and
the void defines an axis extending centrally therethrough.

7. The stent spring of claim 6, wherein the tab is disposed axially between the first structure end and the second structure end.

8. The stent spring of claim 3, wherein:
the first end of the elastic wire engages a first one of the strands; and
the second end of the elastic wire engages a second one of the strands.

9. The stent spring of claim 8, wherein the elastic wire is one of a plurality of elastic wires, and wherein each of the plurality of elastic wires engages an adjacent pair of the strands.

10. The stent spring of claim 8, wherein:
the first one of the strands defines a first groove;
the second one of the strands defines a second groove;

the first end is received within the first groove; and
the second end is received within the second groove.

11. The stent spring of claim 3, wherein the one or more strands define a substantially U-shaped bend at the first structure end, and wherein the elastic wire extends from the substantially U-shaped bend at the first structure end.

12. The stent spring of claim 11, wherein:
the substantially U-shaped bend is one of a plurality of substantially U-shaped bends and the elastic wire is one of a plurality of elastic wires;
a set of first bends of the plurality of substantially U-shaped bends are defined at the first structure end;
a set of second bends of the plurality of substantially U-shaped bends are defined at the second structure end; and
each of the elastic wires extends from one of the first bends or the second bends.

13. The stent spring of claim 12, wherein an opening of the stent spring is defined between each of the first bends and a corresponding one of the second bends.

14. The stent spring of claim 13, wherein the tab is one of a plurality of tabs extending radially inward from the substantially tubular mesh structure, and wherein each of the tabs is disposed axially between the first structure end and the second structure end.

15. The stent spring of claim 2, wherein the elastic wire is substantially U-shaped.

16. The stent spring of claim 1, wherein the elastic wire is positioned on an inner periphery of the stent spring.

17. The stent spring of claim 16, wherein:
the one or more strands define at least one of an upper bend and a lower bend; and
the elastic wire is positioned proximate to the at least one of an upper bend and a lower bend.

18. The stent spring of claim 1, wherein:
a first end of the elastic wire extends through a first groove of the substantially tubular mesh structure and abuts an inner periphery of the stent spring;
a second end of the elastic wire extends through a second groove of the substantially tubular mesh structure and abuts an inner periphery of the stent spring; and
a middle section of the elastic wire is exposed.

19. The stent spring of claim 1, wherein the one or more strands define a plurality of openings.

20. A stent spring for repairing a pipe comprising:
a substantially tubular mesh structure comprising one or more strands, the one or more strands comprising a spring material, wherein the stent spring is expandable and compressible between an expanded configuration and a compressed configuration; and
an elastic wire connected to the one or more strands, the elastic wire configured to increase a flexibility of the stent spring;
wherein:
the elastic wire defines a first end and a second end;
the elastic wire defines a middle section between the first end and second end;
and at least a portion of the middle section is exposed;
the substantially tubular mesh structure defines a first structure end and a second structure end opposite the first structure end;
the elastic wire extends from the substantially tubular mesh structure at one of the first structure end and the second structure end;
the elastic wire is a first elastic wire of a plurality of elastic wires;
the first elastic wire extends from the substantially tubular mesh structure at the first structure end;
the plurality of elastic wires further comprises a second elastic wire extending from the second structure end;
the stent spring defines a void extending from the first structure end to the second structure end;
the void defines an axis extending centrally therethrough;
a tab extends radially inward from the substantially tubular mesh structure; and
a compression mechanism engages the tab to retain the stent spring in the compressed configuration.

21. A stent spring for repairing a pipe comprising:
a substantially tubular mesh structure comprising one or more strands, the one or more strands comprising a spring material, wherein the stent spring is expandable and compressible between an expanded configuration and a compressed configuration; and
an elastic wire connected to the one or more strands, the elastic wire configured to increase a flexibility of the stent spring;
wherein;
the elastic wire defines a first end and a second end;
the elastic wire defines a middle section between the first end and second end;
and at least a portion of the middle section is exposed;
the substantially tubular mesh structure defines a first structure end and a second structure end opposite the first structure end;
the elastic wire extends from the substantially tubular mesh structure at one of the first structure end and the second structure end;
the one or more strands define a substantially U-shaped bend at the first structure end;
the elastic wire extends from the substantially U-shaped bend at the first structure end;
the substantially U-shaped bend is one of a plurality of substantially U-shaped bends and the elastic wire is one of a plurality of elastic wires;
a set of first bends of the plurality of substantially U-shaped bends are defined at the first structure end;
a set of second bends of the plurality of substantially U-shaped bends are defined at the second structure end;
each of the elastic wires extends from one of the first bends or the second bends;
an opening of the stent spring is defined between each the first bends and a corresponding one of the second bends;
a plurality of tabs extends radially inward from the substantially tubular mesh structure; and
each of the tabs is disposed axially between the first structure end and the second structure end.

* * * * *